US012646622B2

(12) United States Patent
Xue et al.

(10) Patent No.: US 12,646,622 B2
(45) Date of Patent: Jun. 2, 2026

(54) DETECTION OF CARDIAC CONDITIONS FROM REDUCED LEAD SET ECG

(71) Applicant: AliveCor, Inc., Mountain View, CA (US)

(72) Inventors: Joel Q. Xue, Germantown, WI (US); Daniel Treiman, San Bruno, CA (US)

(73) Assignee: ALIVECOR, INC., Mountain View, CA (US)

( * ) Notice: Subject to any disclaimer, the term of this patent is extended or adjusted under 35 U.S.C. 154(b) by 328 days.

(21) Appl. No.: 18/132,302

(22) Filed: Apr. 7, 2023

(65) Prior Publication Data

US 2023/0326601 A1 Oct. 12, 2023

Related U.S. Application Data

(60) Provisional application No. 63/328,670, filed on Apr. 7, 2022.

(51) Int. Cl.
| | |
|---|---|
| *A61B 5/346* | (2021.01) |
| *A61B 5/00* | (2006.01) |
| *G06N 3/0464* | (2023.01) |
| *G16H 50/20* | (2018.01) |

(52) U.S. Cl.
CPC ............. *G16H 50/20* (2018.01); *A61B 5/346* (2021.01); *A61B 5/7267* (2013.01); *G06N 3/0464* (2023.01)

(58) Field of Classification Search
CPC ........... A61B 5/327; A61B 5/346; A61B 5/36; A61B 5/7267; G06N 3/0464; G16H 50/20
See application file for complete search history.

(56) References Cited

U.S. PATENT DOCUMENTS

2017/0265765 A1* 9/2017 Baumann ............. A61B 5/7264
2021/0312296 A1 10/2021 Li et al.

FOREIGN PATENT DOCUMENTS

CN 110974214 A 4/2020
WO 2021250553 A1 12/2021

OTHER PUBLICATIONS

PCT International Search Report and Written Opinion from related PCT Application No. PCT/US2023/017966, mailed on Jul. 28, 2023 (15 pages).
International Preliminary Report on Patentability for related PCT Application No. PCT/US2023/017966, mailed on Oct. 17, 2024, 10 pages.

* cited by examiner

*Primary Examiner* — Scott Luan
(74) *Attorney, Agent, or Firm* — Womble Bond Dickinson (US) LLP

(57) ABSTRACT

Embodiments of the present disclosure utilize DNNs for ECG interpretation, where original ECG waveforms are directly ingested by the DNNs using paired interpretation labels for training, without the need for explicatory feature extraction or rule-based criteria.

20 Claims, 15 Drawing Sheets

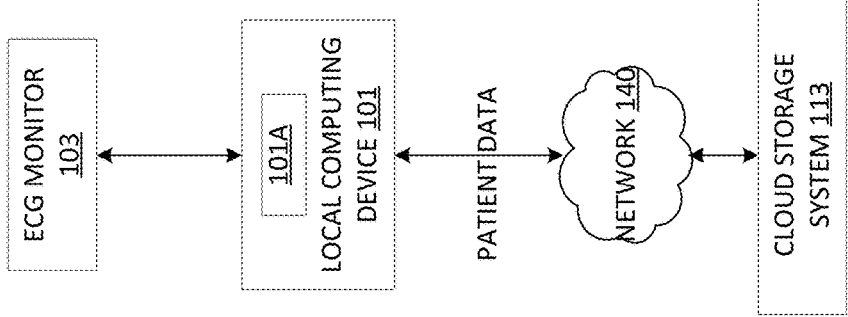
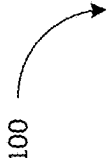
ECG MONITOR 103
LOCAL COMPUTING DEVICE 101
101A
PATIENT DATA
NETWORK 140
CLOUD STORAGE SYSTEM 113
100
*FIG. 1B*

INPUT ECG SIGNALS

LEAD FORMATION LAYER 505

CONVOLUTION LAYERS 510

DENSE LAYERS 515

CLASSIFICATION LAYER 520

PROBABILILTY OF ALL DETERMINATIONS

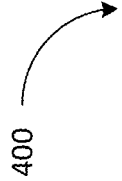
400
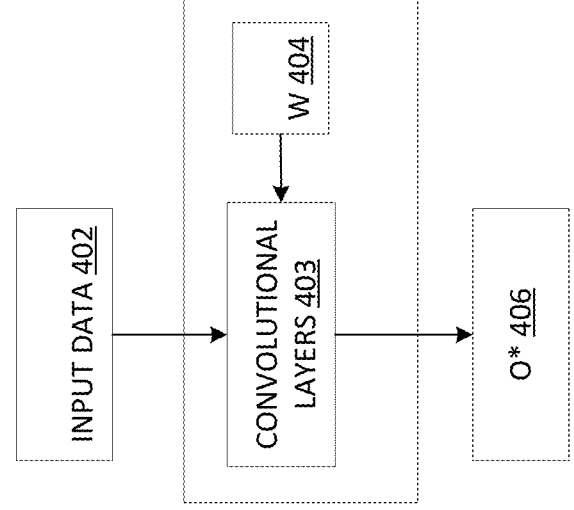
INPUT DATA 402
W 404
CONVOLUTIONAL LAYERS 403
O* 406
*FIG. 5B*

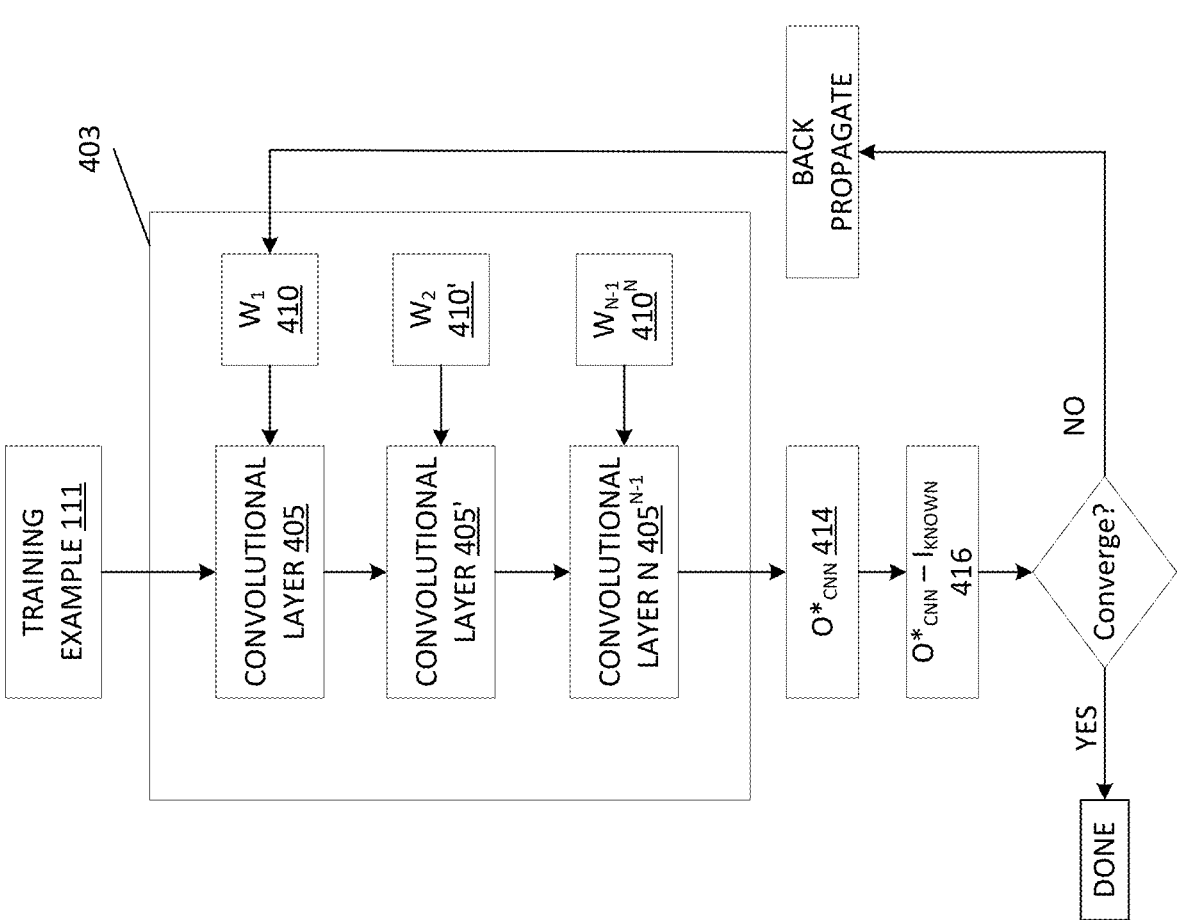
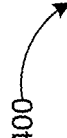
*FIG. 5C*

FIG. 9

PACE RHYTHM CONDITIONS

1. PROBABILITY OF PACE IS HIGH (>0.8)
2. PROBABILITY OF PACE > OTHER RHYTHMS
3. HEART RATE < 80BPM
4. QRS DURATION > 150MS
5. R-R VARIABILITY SMALL

PACE RHYTHM CONFIRMED IF ALL CONDITIONS MET

SINUS RHYTHM CONDITIONS

1. PROBABILITY OF SINUS IS HIGH (>0.7) OR PROBABILITY OF PACE < PROBABILITY OF OTHER RHYTHMS
2. PR INTERVAL > 80MS OR PROBABILITY OF SINUS IS VERY HIGH (>0.95)

SINUS RHYTHM CONFIRMED IF CONDITIONS MET

AFIB/AFLUTTER CONDITIONS

1. PROBABILITY OF AFIB/AFLUTTER IS HIGH (>0.7) AND PROBABILITY OF PACE > OTHER RHYTHMS
2. PR INTERVAL < 30MS PROBABILITY(AFIB) < PROBABILITY(AFLUTTER) -> AFLUTTER

AFIB/AFLUTTER CONFIRMED IF ALL CONDITIONS MET

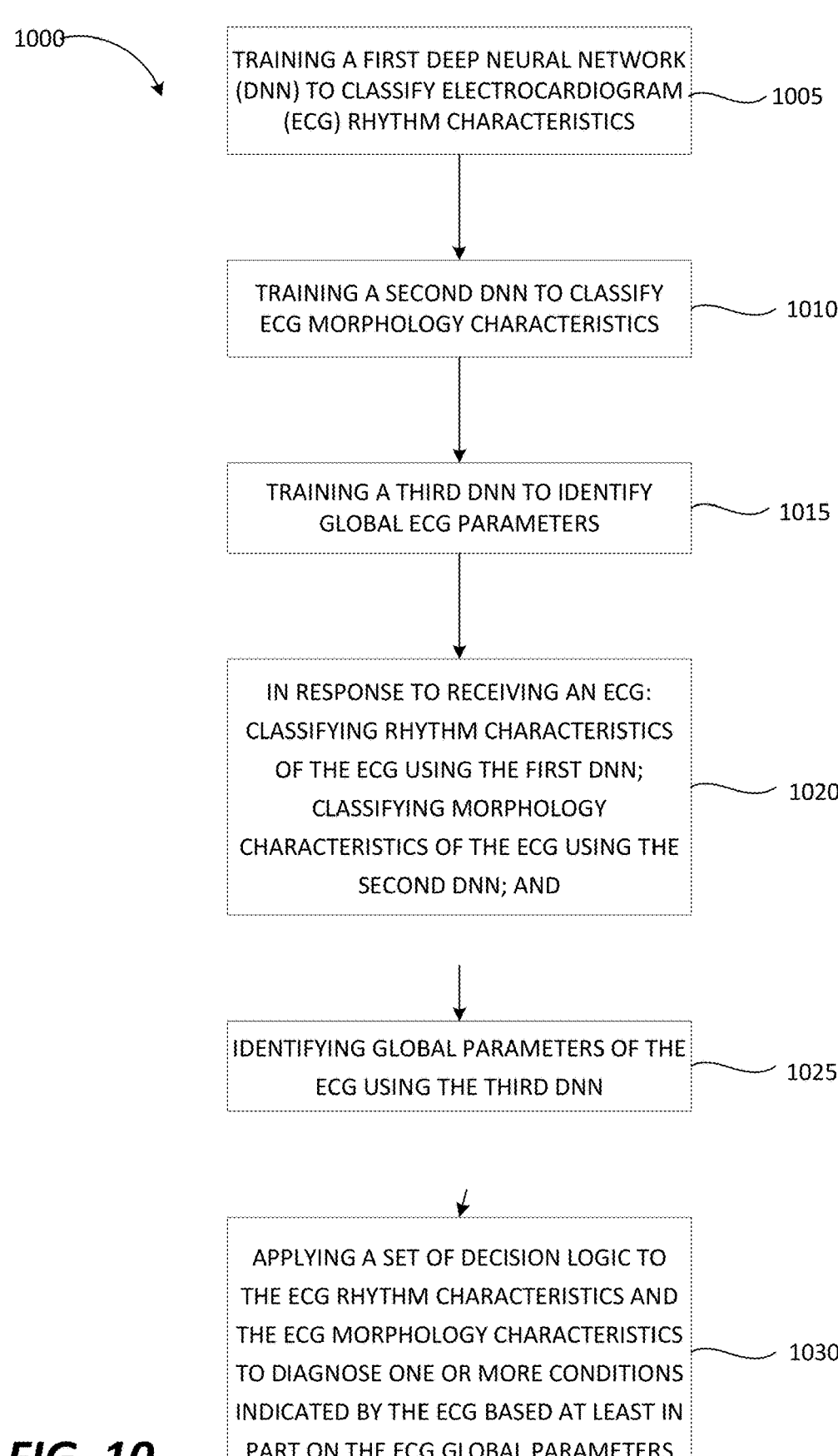

1000

TRAINING A FIRST DEEP NEURAL NETWORK (DNN) TO CLASSIFY ELECTROCARDIOGRAM (ECG) RHYTHM CHARACTERISTICS — 1005

TRAINING A SECOND DNN TO CLASSIFY ECG MORPHOLOGY CHARACTERISTICS — 1010

TRAINING A THIRD DNN TO IDENTIFY GLOBAL ECG PARAMETERS — 1015

IN RESPONSE TO RECEIVING AN ECG: CLASSIFYING RHYTHM CHARACTERISTICS OF THE ECG USING THE FIRST DNN; CLASSIFYING MORPHOLOGY CHARACTERISTICS OF THE ECG USING THE SECOND DNN; AND — 1020

IDENTIFYING GLOBAL PARAMETERS OF THE ECG USING THE THIRD DNN — 1025

APPLYING A SET OF DECISION LOGIC TO THE ECG RHYTHM CHARACTERISTICS AND THE ECG MORPHOLOGY CHARACTERISTICS TO DIAGNOSE ONE OR MORE CONDITIONS INDICATED BY THE ECG BASED AT LEAST IN PART ON THE ECG GLOBAL PARAMETERS — 1030

PROCESSING DEVICE 1102

ECG INTERPRETATION INSTRUCTIONS 1125

MAIN MEMORY 1104

ECG INTERPRETATION INSTRUCTIONS 1125

STATIC MEMORY 1105

NETOWORK INTERFACE DEVICE 1108

NETWORK 1120

BUS 1130

VIDEO DISPLAY 1110

ALPHA-NUMERIC INPUT DEVICE 1112

CURSOR CONTROL DEVICE 1114

SIGNAL GENERATION DEVICE 1115

DATA STORAGE DEVICE 1118

MACHINE-READABLE STORAGE MEDIUM 1128

ECG INTERPRETATION INSTRUCTIONS 1125

DETECTION OF CARDIAC CONDITIONS FROM REDUCED LEAD SET ECG

CROSS-REFERENCE TO RELATED APPLICATIONS

This application claims priority to U.S. Provisional Application No. 63/328,670, filed Apr. 7, 2022 and entitled "SINGLE ALGORITHM DETECTION OF CARDIAC CONDITIONS FROM REDUCED LEAD SET ECG," the disclosure of which is hereby incorporated by reference.

TECHNICAL FIELD

Aspects of the present disclosure relate to diagnosis of cardiac conditions based on an electrocardiogram taken with a reduced lead set, and in particular to algorithmically diagnosing cardiac conditions using a reduced lead set and a single algorithm.

BACKGROUND

Cardiovascular diseases are the leading cause of death in the world. In 2008, 30% of all global death can be attributed to cardiovascular diseases. It is also estimated that by 2030, over 23 million people will die from cardiovascular diseases annually. Cardiovascular diseases are prevalent across populations of first and third world countries alike, and affect people regardless of socioeconomic status.

Arrhythmia is a cardiac condition in which the electrical activity of the heart is irregular or is faster (tachycardia) or slower (bradycardia) than normal. Although many arrhythmias are not life-threatening, some can cause cardiac arrest and even sudden cardiac death. Indeed, cardiac arrhythmias are one of the most common causes of death when travelling to a hospital. Atrial fibrillation (A-fib) is the most common cardiac arrhythmia. In A-fib, electrical conduction through the ventricles of heart is irregular and disorganized. While A-fib may cause no symptoms, it is often associated with palpitations, shortness of breath, fainting, chest pain or congestive heart failure and also increases the risk of stroke. A-fib is usually diagnosed by taking an electrocardiogram (ECG) of a subject. To treat A-fib, a patient may take medications to slow heart rate or modify the rhythm of the heart. Patients may also take anticoagulants to prevent stroke or may even undergo surgical intervention including cardiac ablation to treat A-fib. In another example, an ECG may provide decision support for Acute Coronary Syndromes (ACS) or other cardiac conditions by interpreting various rhythm and morphology conditions, including Myocardial Infarction (MI) and Ischemia.

Often, a patient with A-fib (or other type of arrhythmia) is monitored for extended periods of time to manage the disease. For example, a patient may be provided with a Holter monitor or other ambulatory electrocardiography device to continuously monitor the electrical activity of the cardiovascular system for e.g., at least 24 hours. Such monitoring can be critical in detecting conditions such as acute coronary syndrome (ACS), among others.

The American Heart Association and the European Society of Cardiology recommends that a 12-lead ECG should be acquired as early as possible for patients with possible ACS or other cardiac conditions when symptoms present. Prehospital ECG has been found to significantly reduce time-to-treatment and shows better survival rates. The time-to-first-ECG is so vital that it is a quality and performance metric monitored by several regulatory bodies. According to the national health statistics for 2015, over 7 million people visited the emergency department (ED) in the United States (U.S.) with the primary complaint of chest pain or related symptoms of cardiac conditions. In the US, ED visits are increasing at a rate of or 3.2% annually and outside the U.S. ED visits are increasing at 3% to 7%, annually.

BRIEF DESCRIPTION OF THE DRAWINGS

The described embodiments and the advantages thereof may best be understood by reference to the following description taken in conjunction with the accompanying drawings. These drawings in no way limit any changes in form and detail that may be made to the described embodiments by one skilled in the art without departing from the spirit and scope of the described embodiments.

FIG. 1B is a block diagram that illustrates an example system, in accordance with some embodiments of the present disclosure.

FIG. 5B is a block diagram that illustrates an example convolutional neural network (CNN), in accordance with some embodiments of the present disclosure.

FIG. 5C is a block diagram that illustrates an example training process for a CNN, in accordance with some embodiments of the present disclosure.

FIG. 9 illustrates example conditions for validating classifications of the ECG rhythm classification model of FIG. 6, in accordance with some embodiments of the present disclosure.

FIG. 10 is a flow diagram of a method for training and implementing a reduced lead ECG interpretation model, in accordance with some embodiments of the present disclosure.

DETAILED DESCRIPTION

In the following detailed description of embodiments of the present disclosure, numerous specific details are set forth in order to provide a more thorough understanding of the disclosure. However, it will be apparent to one of ordinary skill in the art that the concepts within the disclosure can be practiced without these specific details. In other instances, well-known features have not been described in detail to avoid unnecessarily complicating the description.

An electrocardiogram (ECG) provides a number of ECG waveforms that represent the electrical activity of a person's heart. An ECG monitoring device may comprise a set of electrodes for recording these ECG waveforms (also referred to herein as "taking an ECG") of the patient's heart. The set of electrodes may be placed on the skin of the patient in multiple locations and the electrical signal (ECG waveform) recorded between each electrode pair in the set of electrodes may be referred to as a lead. Varying numbers of leads can be used to take an ECG, and different numbers and combinations of electrodes can be used to form the various leads. Example numbers of leads used for taking ECGs are 1, 2, 3, 6, and 12 leads.

The ECG waveforms (each one corresponding to a lead of the ECG) recorded by the ECG monitoring device may comprise data corresponding to the electrical activity of the person's heart. A typical heartbeat may include several variations of electrical potential, which may be classified into waves and complexes, including a P wave, a QRS complex, a T wave, and a U wave among others, as is known in the art. Stated differently, each ECG waveform may include a P wave, a QRS complex, a T wave, and a U wave among others, as is known in the art. The shape and duration of these waves may be related to various characteristics of the person's heart such as the size of the person's atrium (e.g., indicating atrial enlargement) and can be a first source of heartbeat characteristics unique to a person. The ECG waveforms may be analyzed (typically after standard filtering and "cleaning" of the signals) for various indicators that are useful in detecting cardiac events or status, such as cardiac arrhythmia detection and characterization. Such indicators may include ECG waveform amplitude and morphology (e.g., QRS complex amplitude and morphology), R wave-ST segment and T wave amplitude analysis, and heart rate variability (HRV), for example.

Figure 1A:
FIG. 1A is a diagram that illustrates an example system, in accordance with some embodiments of the present disclosure.

As noted above, ECG waveforms are generated from measuring multiple leads (each lead formed by a different electrode pair), and the ECG waveform obtained from each different electrode pair/lead may be different/unique (e.g., may have different morphologies/amplitudes). This is because although the various leads may analyze the same electrical events, each one may do so from a different angle. FIG. 1A illustrates a view 105 of an ECG waveform detected by each of 3 leads (I, II, and III) when a 3-lead ECG is taken as well as an exploded view 110 of the ECG waveform measured by lead III illustrating the QRS complex. As shown, the amplitudes and morphologies of the ECG waveform taken from leads I-III are all different, with the ECG waveform measured by lead III having the largest amplitude and the ECG waveform measured by lead I having the smallest amplitude.

There are different "standard" configurations for electrode placement that can be used to place electrodes on the patient. For example, an electrode placed on the right arm can be referred to as RA. The electrode placed on the left arm can be referred to as LA. The RA and LA electrodes may be placed at the same location on the left and right arms, preferably near the wrist in some embodiments. The leg electrodes can be referred to as RL for the right leg and LL for the left leg. The RL and LL electrodes may be placed on the same location for the left and right legs, preferably near the ankle in some embodiments. Lead I is typically the voltage between the left arm (LA) and right arm (RA), e.g. I=LA–RA. Lead II is typically the voltage between the left leg (LL) and right arm (RA), e.g. II=LL–RA. Lead III is the typically voltage between the left leg (LL) and left arm (LA), e.g. III=LL–LA. Augmented limb leads can also be determined from RA, RL, LL, and LA. The augmented vector right (aVR) lead is equal to RA–(LA+LL)/2 or –(I+II)/2. The augmented vector left (aVL) lead is equal to LA–(RA+LL)/2 or I–II/2. The augmented vector foot (aVF) lead is equal to LL–(RA+LA)/2 or II–I/2.

It should be noted that a set of two or more leads may be transformed to generate a full, 12-lead ECG. Such transformation may be performed using a machine learning model (e.g., a neural network, deep-learning techniques, etc.). The machine learning model may be trained using 12-lead ECG data corresponding to a population of individuals. The data, before being input into the machine learning model, may be pre-processed to filter the data in a manner suitable for the application. For example, data may be categorized according to height, gender, weight, nationality, etc. before being used to train one or more machine learning models, such that the resulting one or models are finely-tuned the specific types of individuals. In a further embodiment, the machine learning model may be further trained based on a user's own ECG data, to fine-tune and personalize the model even further to decrease any residual synthesis error.

As discussed herein, a 12-lead ECG should be acquired as early as possible for patients with possible cardiac conditions when symptoms present as prehospital ECG has been found to significantly reduce time-to-treatment and shows better survival rates. In addition, current ambulatory ECG devices such as Holter monitors, are typically bulky and difficult for subjects to administer without the aid of a medical professional. For example, the use of Holter monitors requires a patient to wear a bulky device on their chest and precisely place a plurality of electrode leads on precise locations on their chest. These requirements can impede the activities of the subject, including their natural movement such as bathing and showering. Once an ECG is taken by such devices, the ECG is sent to the subject's physician who then analyzes the ECG waveforms and provides a diagnosis and other recommendations. Currently, this process often must be performed through hospital administrators and health management organizations and many patients do not receive feedback in an expedient manner.

A 12 lead ECG may be administered in a hospital or medical clinic setting in order to detect cardiac conditions, however it would be desirable to have a simpler reduced lead system that could be used at home, or doctor's office, or emergent care, or prehospital in order to detect cardiac conditions. Certain reduced lead (e.g., 6 lead) devices exist that can construct all 12 leads mathematically based on a reduced lead set by either linear or non-linear transformations in order to provide a set of all 12 leads (some are now "synthesized leads"). This synthesized complete 12 lead data can be analyzed by a doctor or a full 12 lead algorithm. Based on existing techniques to reconstruct a full 12 lead set, a natural workflow for an automated system would be the following: 1) use a lead reconstruction algorithm to create a 12-lead set from a reduced lead set (say 4 leads), and then 2) use a pathology classification algorithm to take as input the reconstructed 12 leads and as output provide determinations (classifications) of normal versus various pathologies.

However, there is an intrinsic trade-off with such reduced lead devices as they provide less resolution/ability to detect and discriminate the full range of heart pathologies using the standard 12-lead ECG criteria recommended by cardiology society (ACC/AHA). It would be desirable to have the discriminating ability of a 12 lead system with the simplicity of a reduced set of leads that could be used outside of a hospital (at home, in emergency response, in doctor's offices, etc.) but without the trade-off of sacrificing resolution to discriminate.

A deep neural network (DNN) is a type of model that consists of multiple layers of interconnected nodes, each building upon the previous layer to refine and optimize the prediction or categorization. This progression of computations through the network is called forward propagation. The input and output layers of a deep neural network are called visible layers. The input layer is where the deep learning model ingests the data for processing, and the output layer is where the final prediction or classification is made. A DNN is known to have excellent performance in highly non-linear and highly composite systems (especially when trying to "subsume" multiple algorithmics steps into a single step). A DNN can essentially subsume all algorithm(s) used to make diagnoses based on ECG data into a single mathematical process using a technique called "end-to-end" learning. By utilizing this end-to-end training of what was multiple tasks/ML, models, the resulting DNN can provide high accuracy results, which can often exceed the performance provided by the use of multiple dedicated algorithms.

FIG. 1B shows a system 100 for cardiac disease management. The system 100 may be prescribed for use by a first user e.g., by the first user's physician. Alternatively, system 100 may be used without input from a physician or other third party. The system 100 may comprise a local computing device 101 of the first user. The local computing device 101 may be loaded with a user interface, dashboard, or other sub-system of the cardiac disease management system 100. For example, the local computing device 101 may be loaded with a mobile software application ("mobile app") 101A for interfacing with the system 100. The mobile app 101A may be configured to interface with one or more biometric sensors (e.g., ECG monitor 103) and may comprise software and a user interface for managing biometric data collected by the local computing device 101 from one or more biometric sensors. The local computing device 101 may comprise any appropriate computing device, such as a tablet computer, a smartphone, a server computer, a desktop computer, a laptop computer, or a body-worn computing device (e.g., a smart watch or other wearable), for example. In some embodiments, the local computing device 101 may comprise a single computing device or may include multiple interconnected computing devices (e.g., multiple servers configured in a cluster).

The local computing device 101 may be coupled to one or more biometric sensors. For example, the local computing device 101 may be coupled to an ECG monitor 103 which may comprise a set of electrodes for recording ECG (electrocardiogram) data (also referred to herein as "taking an ECG") of the first user's heart. The ECG data can be recorded or taken using the set of electrodes which are placed on the skin of the first user in multiple locations. The electrical signals recorded between electrode pairs may be referred to as leads and Varying numbers of leads can be used to record the ECG data, and different numbers and combinations of electrodes (placed on the user's arms, legs, and chest) can be used to form the various leads. Example numbers of leads used for taking ECGs are 1, 2, 6, and 12 leads. The electrode placed on the right arm may be referred to as RA. The electrode placed on the left arm may be referred to as LA. The RA and LA electrodes may be placed at the same location on the left and right arms, e.g., near the wrist. The leg electrodes may be referred to as RL for the right leg and LL for the left leg. The RL and LL electrodes may be placed on the same location for the left and right legs, e.g., near the ankle.

Figure 2:
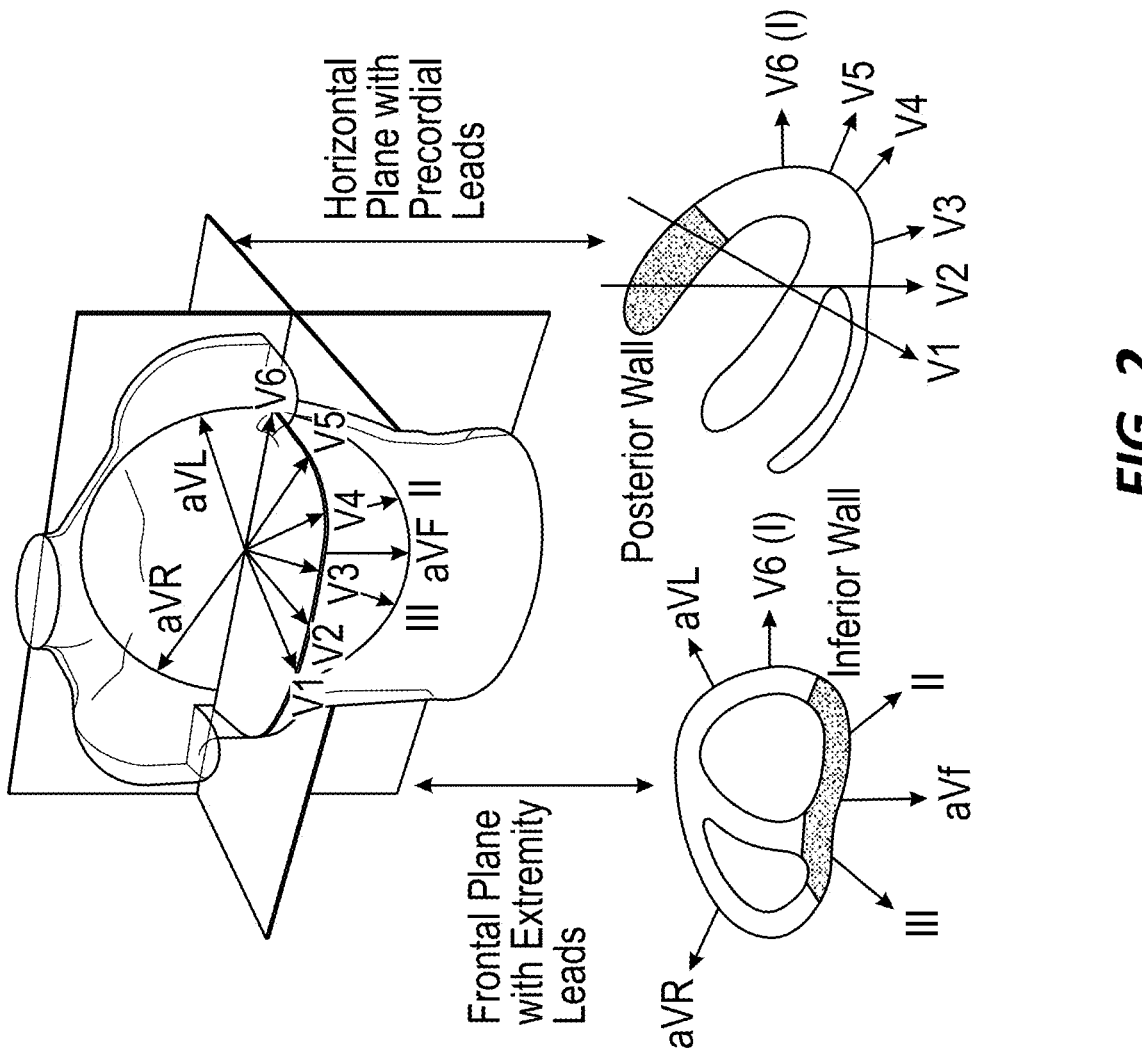
FIG. 2 is a diagram illustrating various leads that an ECG can be comprised of, in accordance with some embodiments of the present disclosure.

FIG. 2 illustrates a single dipole heart model 115 with a 12-lead set comprising the I, II, III, aVR, aVL, aVF, V1, V2, V3, V4, V5, and V6 leads, all represented on a hexaxial system. The heart model 115 assumes a homogeneous cardiac field in all directions that only changes magnitude and direction with the cycle time. As illustrated in FIG. 2, there are 2 orthogonal planes, the frontal plane and the horizontal plane. Inside each plane, there are several leads to cover the whole plane. In the frontal plane, there are 2 independent leads I and II, and 4 other derived leads III, aVR, aVL, and aVF, each 30 degrees apart. The reason the frontal plane has 2 independent leads is that they are far-field leads, each of which can cover a wider perspective but provide less detail, like a wide-angle camera lens. In the horizontal plane, there are normally 6 independent leads which are all closer to the heart than limb leads and may be referred to as near-field leads. Following the same analogy of a camera, the near-field leads may behave like a zoom-lens that covers less perspective, but with more accuracy towards local activity like ischemia and infarction. The two orthogonal planes are related by using a synthetic reference point formed by Leads I & II, called the Wilson-Central-Terminal (WCT). It is defined as RA+LA+RL/3 but given that both Lead I and II are recorded with reference to the RA so that the voltage of the RA can be considered zero, the WCT (VW) can be calculated using the RA as the reference for both Leads I & II (thus, assuming it to have zero potential) as: Lead I+Lead II/3.

Referring back to FIG. 1B, in some embodiments, the ECG monitor 103 may comprise a handheld ECG monitor (such as the KardiaMobile® or KardiaMobile® 6L device from AliveCor® Inc., for example) comprising a smaller number of electrodes (e.g., two, three, four, or any number of electrodes less than twelve). In these embodiments, the electrodes can be used to measure a subset of the leads illustrated in FIG. 2, such as lead I (e.g., the voltage between the left arm and right arm) contemporaneously with lead II (e.g., the voltage between the left leg and right arm), and lead I contemporaneously with lead V2 or another one of the chest leads such as V5. It should be noted that any other combination of leads is possible. If desired, additional leads can then be algorithmically derived (e.g., by the ECG monitor 103 itself or the local computing device 101) from the determined subset of leads. For example, augmented limb leads can also be determined from the values measured by the LA, RA, LL, and RL electrodes. The augmented vector right (aVR) may be equal to RA–(LA+LL)/2 or –(I+II)/2. The augmented vector left (aVL) may be equal to LA–(RA+LL)/2 or I–II/2. The augmented vector foot (aVF) may be equal to LL–(RA+LA)/2 or II–I/2. In some embodiments, the ECG monitor 103 itself or the local computing device 101 may utilize a machine learning (ML) model to derive the full 12 lead set from a measured subset of leads. In some embodiments, the ECG monitor 103 may be in the form of a smartphone, or a wearable device such as a smart watch. In some embodiments, the ECG monitor 103 may be a handheld sensor coupled to the local computing device 101 with an intermediate protective case/adapter.

The ECG data recorded by the ECG monitor 103 may comprise the electrical activity of the first user's heart, for example. A typical heartbeat may include several variations of electrical potential, which may be classified into waves and complexes, including a P wave, a QRS complex, a T wave, and sometimes U wave as known in the art. The shape and duration of the P wave can be related to the size of the user's atrium (e.g., indicating atrial enlargement) and can be a first source of heartbeat characteristics unique to a user.

The QRS complex can correspond to the depolarization of the heart ventricles, and can be separated into three distinct waves—a Q wave, a R wave and a S wave. Because the ventricles contain more muscle mass than the atria, the QRS complex is larger than the P wave. Also, the His/Purkinje system of the heart, which can increase the conduction velocity to coordinate the depolarization of the ventricles, can cause the QRS complex to look "spiked" rather than rounded. The duration of the QRS complex of a healthy heart can be in the range of 60 to 100 milliseconds (ms), but can vary due to abnormalities of conduction. The duration of the QRS complex can serve as another source of heartbeat characteristics unique to a user.

The duration, amplitude, and morphology of each of the Q, R and S waves can vary in different individuals, and in particular can vary significantly for users having cardiac diseases or cardiac irregularities. For example, a Q wave that is greater than $\frac{1}{3}$ of the height of the R wave, or greater than 40 ms (milliseconds) in duration can be indicative of a myocardial infarction and provide a unique characteristic of the user's heart. Similarly, other healthy ratios of Q and R waves can be used to distinguish different users' heartbeats.

The electrical activity of the user US's heart can also include one or more characteristic durations or intervals that can be used to distinguish different users. For example, the electrical activity of the heart may include PR intervals and ST segments as known in the art. A PR interval can be measured from the beginning of P wave to the beginning of a QRS complex. A PR interval can typically last 120 to 200 ms. A PR interval having a different duration can indicate one or more defects in the heart, such as a first degree heart block (e.g., a PR interval lasting more than 200 ms), a pre-excitation syndrome via an accessory pathway that leads to early activation of the ventricles (e.g., a PR interval lasting less than 120 ms), or another type of heart block (e.g., a PR interval that is variable). An ST segment can be measured from a QRS complex to a T wave, for example starting at the junction between the QRS complex and the ST segment and ending at the beginning of the T wave. An ST segment can typically last from 80 to 120 ms, and normally has a slight upward concavity. The combination of the length of ST segment, and the concavity or elevation of ST segment can also be used to generate characteristic information unique to each user's heartbeat.

The ECG monitor 103 may be used by the user to measure their ECG data for analysis as discussed in further detail herein. The ECG monitor 103 may also transmit the measured ECG data and/or the results of the diagnosis analysis (as discussed in further detail herein) to the local computing device 101 by any appropriate wired or wireless connection such as e.g., a Wi-Fi connection, a Bluetooth® connection, a near-field communication (NFC) connection, an ultrasound signal transmission connection, etc.

The ECG data may be continually recorded by the user at regular intervals. For example, the interval may be once a day, once a week, once a month, or some other predetermined interval. The ECG data may be recorded at the same or different times of days, under similar or different circumstances, as described herein. The ECG data may also be recorded at the same or different times of the interval (e.g., the ECG data may be captured asynchronously). Alternatively, or additionally, the ECG data can be recorded on demand by the user at various discrete times, such as when the user feels chest pains or experiences other unusual or abnormal feelings, or in response to an instruction to do so from e.g., the user's physician. In another embodiment, ECG data may be continuously recorded over a period of time.

Each ECG data recording may be time stamped and may be annotated with additional data by the user or health care provider to describe user characteristics. For example, the local computing device 101 (e.g., the mobile app 101A thereof) may include a user interface for data entry that allows the user to enter their user characteristics. Examples of user characteristics may include age, sex, race, ethnicity, relevant medical history, location, diet (e.g., food/drink habits), medication/drug consumption, exercise patterns, sleep/rest patterns, feelings of stress, anxiety, pain or other unusual or abnormal feelings, activities performed before, during, or after the data recording, or any other user specific circumstance or factor that may affect the user's ECG data. The local computing device 101 may append the user characteristics to the ECG data and store the ECG data and user characteristics for further analysis (e.g., ECG interpretation). Alternatively, the local computing device 101 may transmit the ECG data and user characteristics (collectively referred to as user data) to the cloud storage system 113. Because the user data is time stamped or tagged, the ECG data can be matched or correlated with an activity or circumstance of interest. As described in further detail herein, this also allows for comparison of the ECG data before, after and during the activity or circumstance of interest so that the effect on the ECG data can be determined and accounted for during further analysis.

When the user data is transmitted by the local computing device 101 to the cloud storage system 113 for storage and analysis, such transmission can be real-time, at regular intervals such as hourly, daily, weekly and/or any interval in between, or can be on demand. The local computing device 101 and the cloud storage system 113 may be coupled to each other (e.g., may be operatively coupled, communicatively coupled, may communicate data/messages with each other) via network 140. Network 140 may be a public network (e.g., the internet), a private network (e.g., a local area network (LAN) or wide area network (WAN)), or a combination thereof. In one embodiment, network 140 may include a wired or a wireless infrastructure, which may be provided by one or more wireless communications systems, such as a Wi-Fi hotspot connected with the network 140 and/or a wireless carrier system that can be implemented using various data processing equipment, communication towers (e.g., cell towers), etc. The network 140 may carry communications (e.g., data, message, packets, frames, etc.) between the local computing device 101 and the cloud storage system 113.

The user data accumulated over time for a particular user may form a time series health record for that particular user. The cloud storage system 113 may comprise any suitable type of computing device or machine that has a programmable processor including, for example, a server computer, a desktop computer, laptop computer, tablet computer, smartphone, etc. In some embodiments, the cloud storage system 113 may comprise a single computing device or may include multiple interconnected computing devices (e.g., multiple servers configured in a cloud storage cluster).

Figure 3:
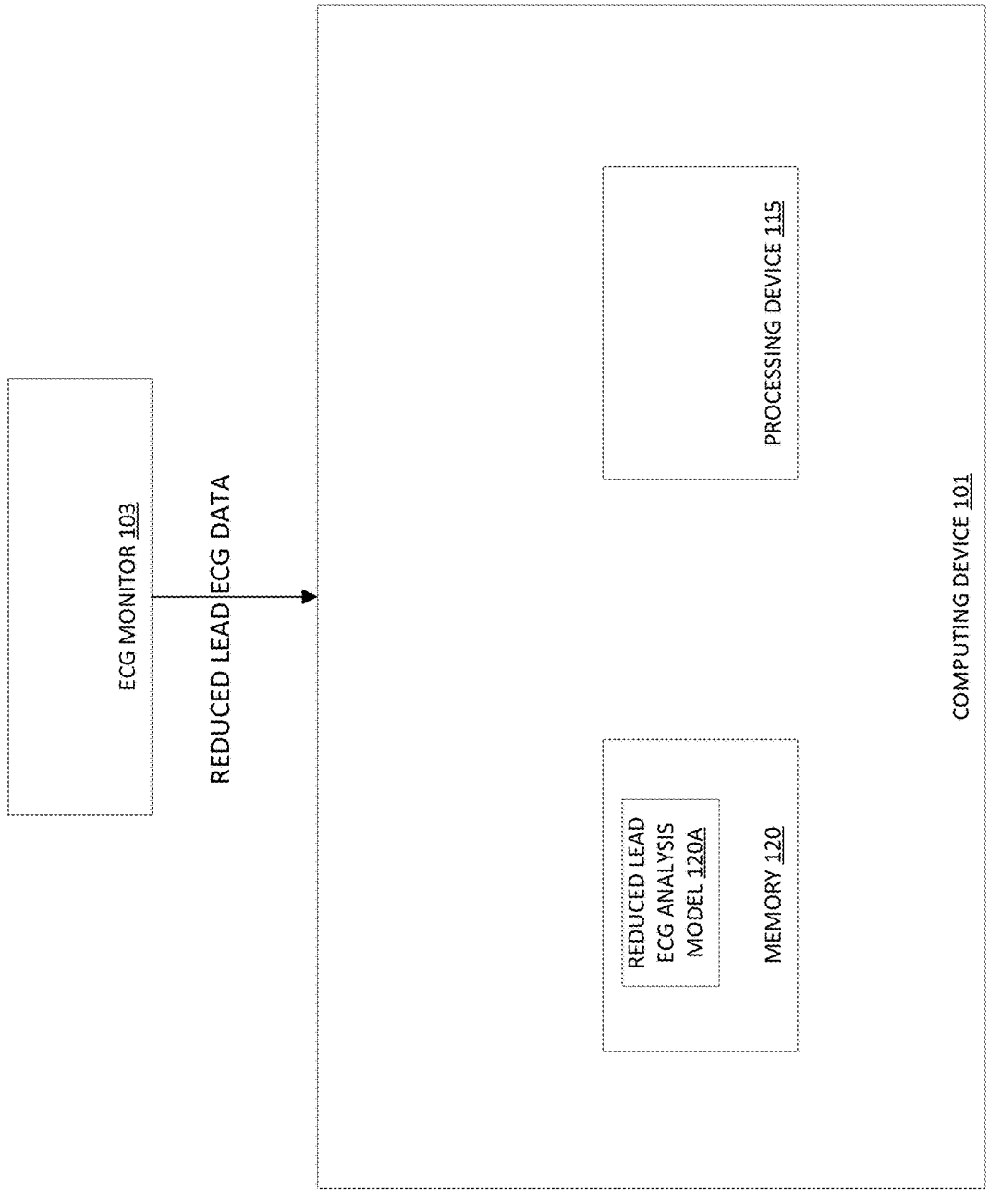
FIG. 3 is a block diagram that illustrates an example system, in accordance with some embodiments of the present disclosure.

FIG. 3 illustrates a hardware block diagram of the computing device 101. The computing device 101 may include hardware such as processing device 115 (e.g., processors, central processing units (CPUs)), memory 120 (e.g., random access memory (RAM)), storage devices (e.g., hard-disk drive (HDD), solid-state drive (SSD), etc.), and other hardware devices (e.g., sound card, video card, etc.). In some embodiments, memory 120 may be a persistent storage that is capable of storing data. A persistent storage may be a local storage unit or a remote storage unit. Persistent storage may be a magnetic storage unit, optical storage unit, solid state storage unit, electronic storage units (main memory), or similar storage unit. Persistent storage may also be a mono-lithic/single device or a distributed set of devices. Memory 120 may be configured for long-term storage of data and may retain data between power on/off cycles of the computing device 101. The memory 120 may store the user data accumulated over time for the user as well as a multitude of other users. The memory 120 may further include a reduced lead ECG analysis model 120A that is configured to analyze reduced lead ECG data of the user that is measured each time an ECG is performed to determine whether the user is experiencing a cardiac condition as discussed in further detail herein.

As discussed herein, mobile ECG monitors attempt to simplify the process of taking an ECG by using a reduced set of leads e.g., any number of leads less than 12. However, such implementations must intrinsically sacrifice resolution or discriminating ability when detecting the full range of heart pathologies for the convenience of a reduced lead set. Prior work has tried to construct all 12 leads mathematically based on a reduced lead set by either linear or non-linear transformations in order to provide a set of all 12 leads (some are now "synthesized leads") and this synthesized complete 12 lead data can be analyzed by a doctor or a full 12 lead algorithm. Based on this prior work to reconstruct a full 12 lead set, a natural workflow for an ML model implemented by the mobile ECG device would also involve multiple layers including for example: 1) use a lead recon-struction algorithm to create a 12-lead set from a reduced lead set (say 4 leads), and 2) use a pathology classification algorithm to take as input the reconstructed 12 leads and provide as output provide determinations (classifications) of normal versus various pathologies. However, the application of reduced lead 12-lead sets and synthesized leads can be limited because ECG criteria that is developed with standard 12-lead ECGs is applied for abnormal case detection and interpretation. There is no specific criteria that has been developed or recommended by ACC/AHA for the reduced lead sets. This results in gaps in accuracy for such synthe-sized leads, especially in localized STEMI situations.

In addition, solving the problem of providing accurate readings of reduced lead ECGs requires an ML model architecture consisting of different layers (e.g., preprocess-ing, feature extraction, optimization, prediction, decision making) including lead reconstruction and pathology clas-sification that each process input data in a pipe-lined fashion. However, such a multi-layer approach may provide less than ideal results due to the complexity of the model. For example, such a multi-layer architecture requires that each layer be optimized separately under different criteria.

A deep neural network (DNN) is a type of model that consists of multiple layers of interconnected nodes, each building upon the previous layer to refine and optimize the prediction or categorization. This progression of computa-tions through the network is called forward propagation. The input and output layers of a deep neural network are called visible layers. The input layer is where the deep learning model ingests the data for processing, and the output layer is where the final prediction or classification is made. For example, we may have a set of photos of different pets, and may wish to categorize by "cat", "dog", "hamster", etc. Deep learning algorithms can determine which features (e.g., ears) are most important to distinguish each animal from another. In machine learning, this hierarchy of features is established manually by a human expert. Then, through the processes of gradient descent and backpropagation, the DNN adjusts and fits itself for accuracy, allowing it to make predictions about a new photo of an animal with increased precision. Back-propagation involves fine-tuning the weights of a neural net based on the error rate (i.e., loss) obtained in the previous epoch (i.e. iteration). Proper tuning of the weights ensures lower error rates, making the model reliable by increasing its generalization.

DNNs can also be trained using end-to-end learning, which takes advantage of a DNNs structure, which is composed of several layers, to solve complex problems. For ECG processing, the input end is an ECG waveform, and the output end are the classification results. Each DNN layer (or group of layers) can specialize to perform intermediate tasks necessary for such problems. For example, the convolution layers (CNN) of the DNN model can extract ECG features automatically. But those features are mostly distributed in a vector of the intermediate output layer, called flatten layer, at the end of CNN blocks. The elements in the flatten layer are also called embedding variables, which can be used either for classification of the rhythm and morphology interpretations, or regression to predict ECG measurements like PR interval, QRS duration, and QT interval. End-to-end learning refers to training a possibly complex learning system represented by a single model (specifically a DNN) that represents the complete target system, bypassing the intermediate layers usually present in traditional pipeline designs. Stated differently, when two or more ML models are serving as components to a larger architecture, a DNN may be trained in an end-to-end manner which involves simultaneously training all components (i.e., training it as a single network).

Embodiments of the present disclosure utilize DNNs for ECG interpretation, where original ECG waveforms are directly ingested by the DNNs using paired interpretation labels for training, without the need for explicatory feature extraction or rule-based criteria. As discussed in further detail herein, the embodiments of the present disclosure differ from conventional expert system-based criteria since DNN models play a significant role in the overall ECG classification and ECG interpretation process.

FIG. 4A illustrates the reduced lead ECG analysis model 120A (hereinafter referred to as interpretation model 120A). The interpretation model 120A includes a data conditioning stage 130, a model analysis stage 140, and a final determi-nation stage 150. The data conditioning stage 130 may include filtering and signal processing functions, as well as a down sampling module 131, a lead conversion module 132, and a median beats generation module 133. For example, the interpretation model 120A may receive as input (e.g., from ECG monitor 103), a first 4-lead ECG signal including leads, [I, II, v2, v4] and a second 4-lead ECG signal including leads [I, II, v1, v4], where the signal from each lead is 10 seconds. Although illustrated as using 10 second samples of leads [I, II, v1/v2, v4], this is for example purposes and is not a limitation. Indeed, any appropriate set of input leads may be used and each lead's signal may have any appropriate duration. The down sampling module 131 may down-sample each input 4-lead ECG signal to 150 Hz, while the lead conversion module 132 may determine another 4 limb leads, [III, aVR, aVL, aVF] using conventional lead reconstruction algorithms. The lead conversion module 132 may add the algorithmically reconstructed leads to each of the 4-lead ECG signals resulting in two 8 lead ECG signals. A first 8 lead ECG signal may include leads [I, II, III, v2, v4, aVR, aVL, aVF] while the second 8 lead ECG signal may include leads [I, II, III, v1, v4, aVR, aVL, aVF].

Training ML models to classify ECG signals requires determining the underlying characteristics of the ECG signals. The model analysis stage 140 may include ML models to identify the underlying characteristics of the input ECG signals including ECG rhythm patterns and ECG waveform morphology/shape patterns. Each of the ML models in the model analysis stage 140 may be any appropriate deep neural network (DNN) model such as a convolutional neural network (CNN) or any other appropriate DNN. Determining ECG rhythm patterns requires capturing the sequential characteristics of the ECG rhythm patterns, which in turn requires detecting those characteristics effectively. Thus, the model analysis stage 140 may include for each of the 8 lead ECG signals, an ECG rhythm classification model 141. Stated differently, each 8 lead ECG signal may serve as an input to a corresponding ECG rhythm classification model 141. An adequate time window for the input data (in this case, a 10 second window for the two 8 lead ECG signals) should be used to allow for the sequential characteristics of rhythm patterns to be detected without further features detection.

Besides rhythm patterns, waveform morphology/shape patterns are another major ECG characteristic, and are usually detected with ECG amplitude and duration/intervals. For waveform morphology, different types of representative beats of a data series (e.g., median beats, average beats of multiple ECG cycles) can simplify a waveform morphology detection model and speed up the training, while also improving the classification accuracy. Thus, a median beats generation module 133 may determine the median beats of the first and second 8 lead ECG signals resulting in first and second median beat 8 lead signals respectively. The model analysis stage 140 may include for each of the median beat 8 lead signals, an ECG morphology model 142. Stated differently, each median beat 8 lead signal may serve as an input to a corresponding ECG morphology ML model 142. The model analysis stage 140 may further include a global ECG measurements model 143 for detecting global ECG parameters including e.g., PR interval, QRS duration, and QT interval. The embodiments of the present disclosure are described with respect to only the first 8 lead ECG signal and the corresponding ECG rhythm classification model 141 and ECG morphology ML model 142, however this is for ease of description and each 8 lead ECG signal may have its own DNN models that may form corresponding classifications as described in further detail herein.

The final determination stage 150 may include final ECG rhythm logic 151 and final ECG morphology logic 152, each of which may include some simple logic to validate a classification by a corresponding DNN. The final analysis combines all DNN output and ECG measurements like PR, QRSD, QT interval, ST levels to refine the classifications. The outputs of the final determination stage 150 may be probabilities predicting the likelihood of various (often times hard-to-discriminate) heart pathologies (or an indication that the user's cardiac health is normal).

Figure 5A:
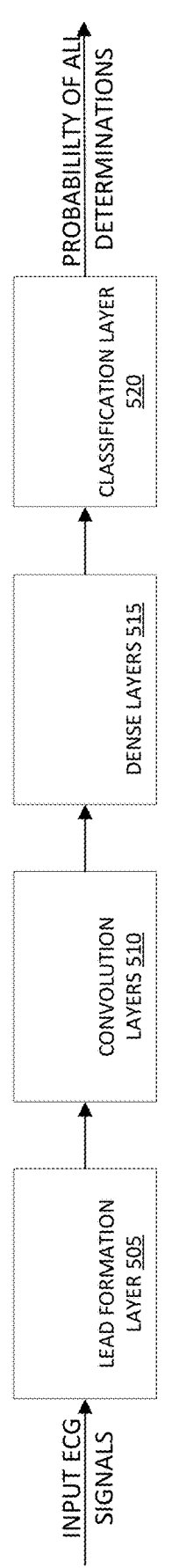
FIG. 5A is a block diagram illustrating the basic structure of a deep neural network (DNN), in accordance with some embodiments of the present disclosure.

FIG. 5A illustrates the general structure 500 of each model 141, 142 and 143 used in the model analysis stage 140. Each model may include 4 major components. The first component may be a lead formation layer 505 which reformats the leads of the 8 lead ECG signal (or the median beat 8 lead signal), to a format needed for training the model. The second component may be a set of convolution layers 510, which may include a number (e.g., 5-8) of CNN blocks with different numbers of filters for each block. The third component may be a set of dense layers 515, which reshape the multi-filter output of the final convolution layer to a flattened layer and pass the results to the next dense layers with full connections, meaning each unit of the previous layer is connected to all units of the next layer. The fourth component may be a classification layer 520, which generates a probability for each determination.

FIG. 5B illustrates an example of a DNN 400 that could be used in conjunction with some embodiments of the present disclosure. The DNN 400 may comprise a trained CNN model that takes input data 402 (e.g., user data) into convolutional layers (aka hidden layers) 403, applies a series of trained weights or filters 404 to the input data 406 in each of the convolutional layers 403. The output of the first convolutional layer is an activation map (not shown), which is the input to the second convolution layer, to which a trained weight or filter (not shown) is applied, where the output of the subsequent convolutional layers results in activation maps that represent more and more complex features of the input data to the first layer. After each convolutional layer a non-linear layer (not shown) is applied to introduce non-linearity into the problem, which nonlinear layers may include an activation function such as tan h, sigmoid or ReLU. In some cases, a pooling layer (not shown) may be applied after the nonlinear layers, also referred to as a downsampling layer, which takes a filter and stride of the same length and applies it to the input, and outputs the maximum number in every sub-region the filter convolves around. Other options for pooling are average pooling and L2-norm pooling. The pooling layer reduces the spatial dimension of the input volume reducing computational costs and to control over-fitting. The final layer(s) of the network is a fully connected layer, which takes the output of the last convolutional layer and outputs an n-dimensional output vector representing the quantity to be predicted, e.g., probabilities of LVH diagnosis and (if applicable) severity of LVH. This may result in predictive output 406 (O*), e.g., this user is likely suffering from stage 2 LVH. The trained weights 404 may be different for each of the convolutional layers 403, as will be described more fully below.

FIG. 5C demonstrates the process of training the DNN 400 (without the dense layers and classification layer shown for simplicity). In FIG. 5C convolution layers 403 are shown as individual convolution layers 405, 405' to convolution layer $(405)^{n-1}$ and the final nth layer is a fully connected layer. It will be appreciated that last layers may be more than one fully connected layer. A training example 411 is input into convolution layers 403, a nonlinear activation function (not shown) and weights 410, 410' through 410" are applied to training example 411 in series, where the output of any convolution layer is input to the next layer, and so on until the final nth fully connected layer $(405)^{n-1}$ produces output 414. The output or prediction 414 (*) is compared against training example 411 (e.g., Wide QRS Tachycardia) resulting in difference 416 between output or prediction 414 and training example 411 (also shown as $I_{known}$ in FIG. 6B). If the difference or loss 416 is less than some preset loss (e.g., output or prediction 414 predicts the user is suffering from Wide QRS Tachycardia with the requisite level of accuracy), the DNN model is converged and considered trained.

If the DNN 400 has not converged, using the technique of backpropagation, weights 410 and $410^{n-1}$ through $410^n$ are updated in accordance with how close the prediction is to the known input. The skilled artisan will appreciate that methods other than back propagation may be used to adjust the weights. A second training example (e.g., different user data) may be input and the process is repeated again with the updated weights, which are then updated again and so on until the nth training example (e.g., nth user data) has been input. This is repeated over and over with the same n-training examples until the DNN model is trained or converges on the correct outputs for the known inputs. Once the DNN model is trained, weights 410 through $410^n$ are fixed and used in trained ECG rhythm classification model 141. As discussed herein, there are different weights for each convolutional layer 403 and for each of the fully connected layers. The trained ECG rhythm classification model 141 is then fed user data to determine or predict that which it is trained to predict/identify (e.g., rhythm classification), as described herein in further detail.

Figure 6:
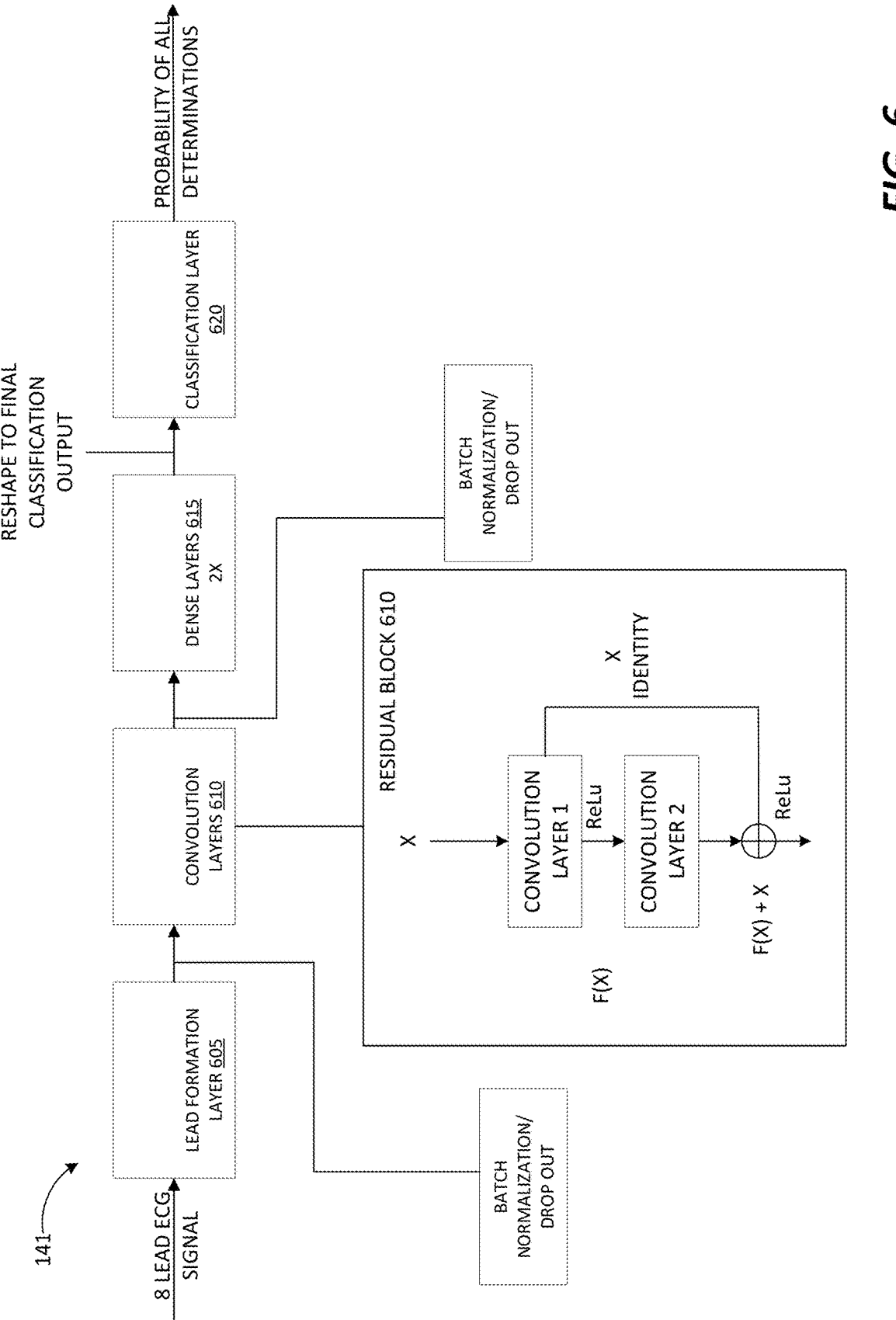
FIG. 6 is a block diagram illustrating an example ECG rhythm classification model, in accordance with some embodiments of the present disclosure.

FIG. 6 illustrates a detailed structure of the ECG rhythm classification model 141. The convolution layers 610 may utilize a residual block structure that utilizes combinations of convolution layers and skip layers. A skip layer (also referred to as a skip connection or shortcut connections) may enable a residual block in the deep learning models to address the problem of vanishing and exploding gradients, which can occur when training very deep neural networks. This is done by adding the input of a layer directly to the output of one or more subsequent layers, creating a "shortcut" for the gradient to flow through. As a result, different parts of the convolution layers 610 will be trained at different rates for different training data points based on how the error flows backward through the layers of the convolution layers 610. FIG. 6 illustrates a residual block 610A, where a skip layer is used to skip the training of the convolution layer 2 during learning of an identity function X. ReLu may represent a nonlinear activation function.

In addition to the residual blocks, the ECG rhythm classification model 141 may include 2 dense layers 615 and 1 classification layer 620. In some embodiments, the ECG rhythm classification model 141 may further include a batch normalization layer and dropout layer for every residual block and dense layer to improve its robustness or generalization once it is trained (not every batch normalization and dropout layer shown in FIG. 6). The ECG rhythm classification model 141 is designed to classify rhythm determinations, examples of which are shown in table 1 (below). The classification layer 620 output may have both positive and negative probabilities for each determination. In some embodiments, for each of the 8 lead ECG signals (downsampled to 150 Hz), 9.5 seconds out of the 10 seconds of data is used for the input and the remaining 0.5 seconds of data may be used for augmentation with a time-shifting technique (random data shifting). This random data shifting is one of the data augmentation methods used to improve the generalization of the trained DNN models, which will result in the DNN models being less sensitive to the start and the end times of the input ECG rhythm data.

TABLE 1

| order | Determinations |
|---|---|
| 1 | Normal Sinus Rhythm |
| 2 | Sinus rhythm |
| 3 | Atrial fibrillation |
| 4 | Atrial flutter |
| 5 | $1^{st}$ degree AV block |
| 6 | $2^{nd}$ degree AV block (mobiz 1) |
| 7 | $2^{nd}$ degree AV block (mobiz 2) |
| 8 | $3^{rd}$ degree AV block (Complete AV block) |
| 9 | Wide QRS Tachycardia |
| 10 | Sinus Arrythmia |
| 11 | Marked Sinus Arrythmia |
| 12 | Paced rhythm |
| 13 | Marked bradycardia |
| 14 | Junctional rhythm |
| 15 | Ectopic Atrial rhythm |
| 16 | Super Ventricular Tachycardia |
| 17 | Undetermined rhythm |
| 18 | Sinus Tachycardia |
| 19 | Bigeminy |
| 20 | PVCs |

The ECG rhythm classification model 141 may be trained using any sufficiently large training data set. For example, the training data set may include 1 million labeled ECGs, with another 250K labeled ECGs for use as an independent test set. In the example of FIG. 6A, the batch size is 512, the learning rate is 0.001, and the drop rate 0.05. A total of 20 epochs are set. The final model is selected from the smallest validation error. A training weight matrix is used for balancing a large difference in prevalence among all determinations. For the lower prevalence determinations, a higher weight is used when the training error is backpropagated.

Figure 7A:
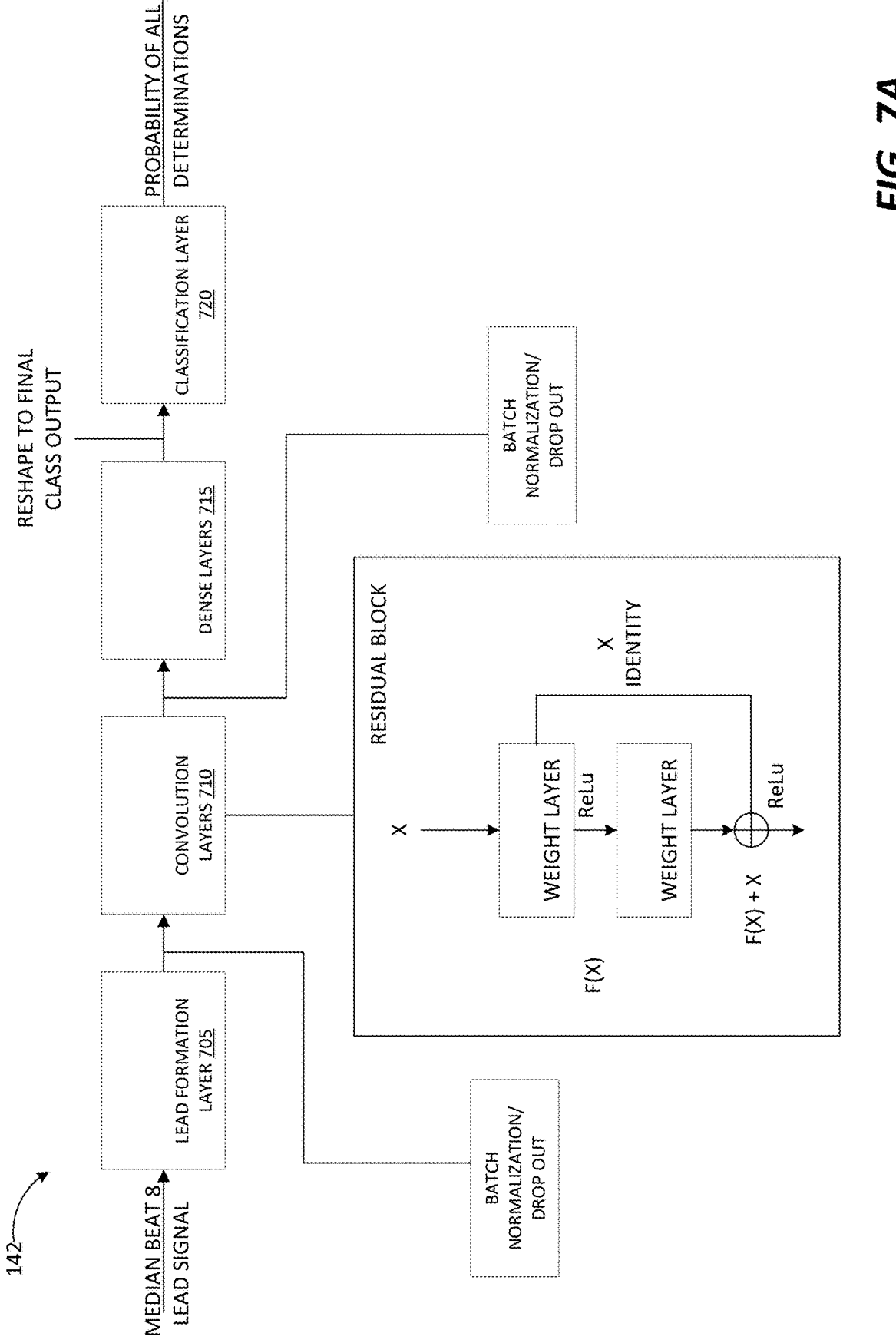
FIG. 7A is a block diagram illustrating an example ECG morphology classification model, in accordance with some embodiments of the present disclosure.

FIG. 7A illustrates a detailed structure of the ECG morphology model 142. The ECG morphology model 142 may capture morphology changes for each lead and relative changes from lead to lead, referred to as changes in the spatial domain. The ECG morphology model 142 may have a similar model structure as the ECG rhythm classification model 141, but with a smaller lead formation layer and fewer residual block layers, since the median beat 8 lead signal has a much shorter length than the 10 second duration of the 8 lead ECG signal input to the ECG rhythm classification model 141. In addition, all median beats are relatively aligned around their QRS onset. Another important design consideration for the Morphology model QRS region, is that the variations along the time axis are relatively smaller than rhythm signals.

To capture the spatial domain changes, the ECG morphology model 142 may form an ECG imaging by laying out of all the leads in a 2-D matrix/image pattern with the X-axis as time and the Y-axis as a lead order of [aVL, I, aVR, II, aVF, III, v2, v4], where the limb leads are reordered in a so-called Cabrera sequence. The ECG morphology model 142 may process the 2-D ECG signal matrix with a 2-D convolutional filter like in image classification cases. This method is more effective than applying multiple 1-D convolutional filters to each lead separately, which has been used by most other ECG training models. Since ECG is a projection of heart's electrical depolarization and repolarization process to the torso, a spatial 2-D signal matrix can capture this projection more effectively. Therefore, 2-D convolutional modes are applied to this ECG image input.

Figures 7B, 7C:
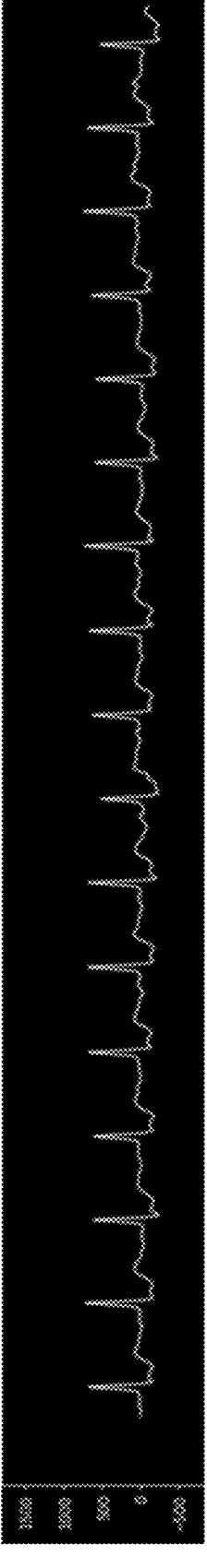
FIGS. 7B and 7C are block diagrams illustrating an ECG signal and a median beat of the ECG signal respectively, in accordance with some embodiments of the present disclosure.

As discussed herein, the median beats generation module 133 may generate the median beat 8 lead signal based on the 8 lead ECG signal. More specifically, the median beats generation module 133 may form a QRS detection function, perform beat detection and classification, perform beat alignment, and calculate the median and average beats from the dominant beat type. FIG. 7B shows an example 8 lead ECG signal and FIG. 7C shows the median beat of the example 8 lead ECG signal. As can be seen, the ECG morphology features are captured in the median beat while the data length is much shorter.

The ECG morphology model 142 may be trained with the same training data set as the ECG rhythm classification model 141 (which may include median beat data for each training ECG). In the example of FIG. 6A, the batch size is 512, the learning rate is 0.001, and the drop rate 0.05. A total of 20 epochs are set. The final model is selected from the smallest validation error. A morphology training weight matrix is also used for balancing a large difference in prevalence among all determinations. For the lower prevalence determinations, a higher weight is used when the training error is backpropagated. The ECG morphology model 142 is designed to classify ECG morphology determinations, examples of which are shown in table 2 (below). The classification layer of the ECG morphology model 142 has both positive and negative probabilities for each determination.

TABLE 2

| order | Determinations |
| --- | --- |
| 1 | Right bundle branch block (RBBB) |
| 2 | Left bundle branch block (LBBB) |
| 3 | Other Intra-Ventricular block |
| 4 | Left Ventricle Hypertrophy (LVH) |
| 5 | Right Ventricle Hypertrophy (RVH) |
| 6 | Right Atrial Enlargement (RAE) |
| 7 | Right Atrial Enlargement (RAE) |
| 8 | Anterior MI old |
| 9 | Inferior MI old |
| 10 | Lateral MI old |
| 11 | Septal MI old |
| 12 | Anterior MI acute |
| 13 | Inferior MI acute |
| 14 | Lateral MI acute |
| 15 | Septal MI acute |
| 16 | Anterior Ischemia |
| 17 | Inferior Ischemia |
| 18 | Lateral Ischemia |
| 19 | Septal Ischemia |
| 20 | Acute pericarditis |
| 21 | Early Repolarization |
| 22 | Prolonged QT |
| 23 | Paced ECG |
| 24 | Wolff-Parkinson-White (WPW) |
| 25 | Normal ECG |

The global ECG measurements model 143 may measure ECG global parameters including PR interval, QRS duration, QT interval, and heart rate. These parameters are referred to as ECG global measurements because they are not lead-specific and are often estimated based on a combination of multiple leads. These parameters are often detected with complicated signal processing and feature detection algorithms based on domain knowledge. However, embodiments of the present disclosure estimate these ECG parameters using a deep learning model (the global ECG measurements model 143) applied to the median beat 8 lead signal generated from the 8 lead ECG signal. Because the ECG global parameters are closely related to ECG morphology, the global ECG measurements model 143 can be trained to perform a regression of the median beat 8 lead ECG signal to detect these parameters. Another aim of training the global ECG measurements model 143 is to also be able to identify the absence of a valid P wave as in atrial fibrillation cases.

Figure 8:
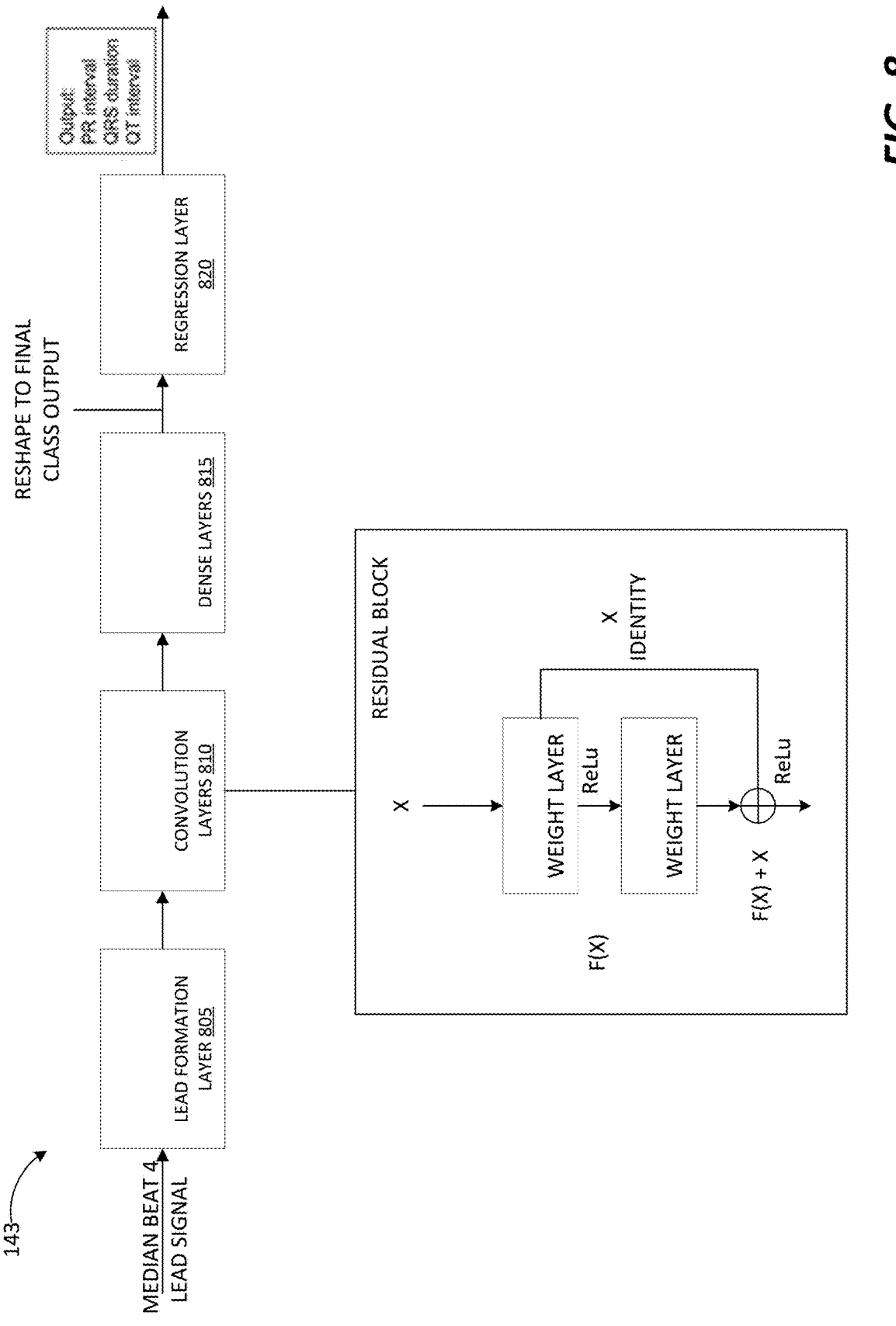
FIG. 8 is a block diagram illustrating an example global ECG feature model, in accordance with some embodiments of the present disclosure.

FIG. 8 illustrates a detailed structure of the global ECG measurements model 143. The structure of the global ECG measurements model 143 is like the structure of the ECG morphology model 142 except the final classification layer of the global ECG measurements model 143 is replaced by a regression layer 820. In addition, the global ECG measurements model 143 does not have the batch normalization layers of the ECG morphology model 142 since they are more useful for classification than for regression. The global ECG measurements model 143 may receive as input a median beat 4 lead signal based on the lead set [I, II, v2, v4]. More specifically, the median beats generation module 133 may determine the median beats for each lead of the lead set [I, II, v2, v4] as discussed hereinabove and provide this median beat 4 lead signal to the global ECG measurements model 143. The global ECG measurements model 143 is trained to output three intervals: PR interval, QRS duration, and QT interval by minimizing the absolute error between labeled (physician-estimated) intervals from the training data and the model-estimated intervals.

Figure 4:
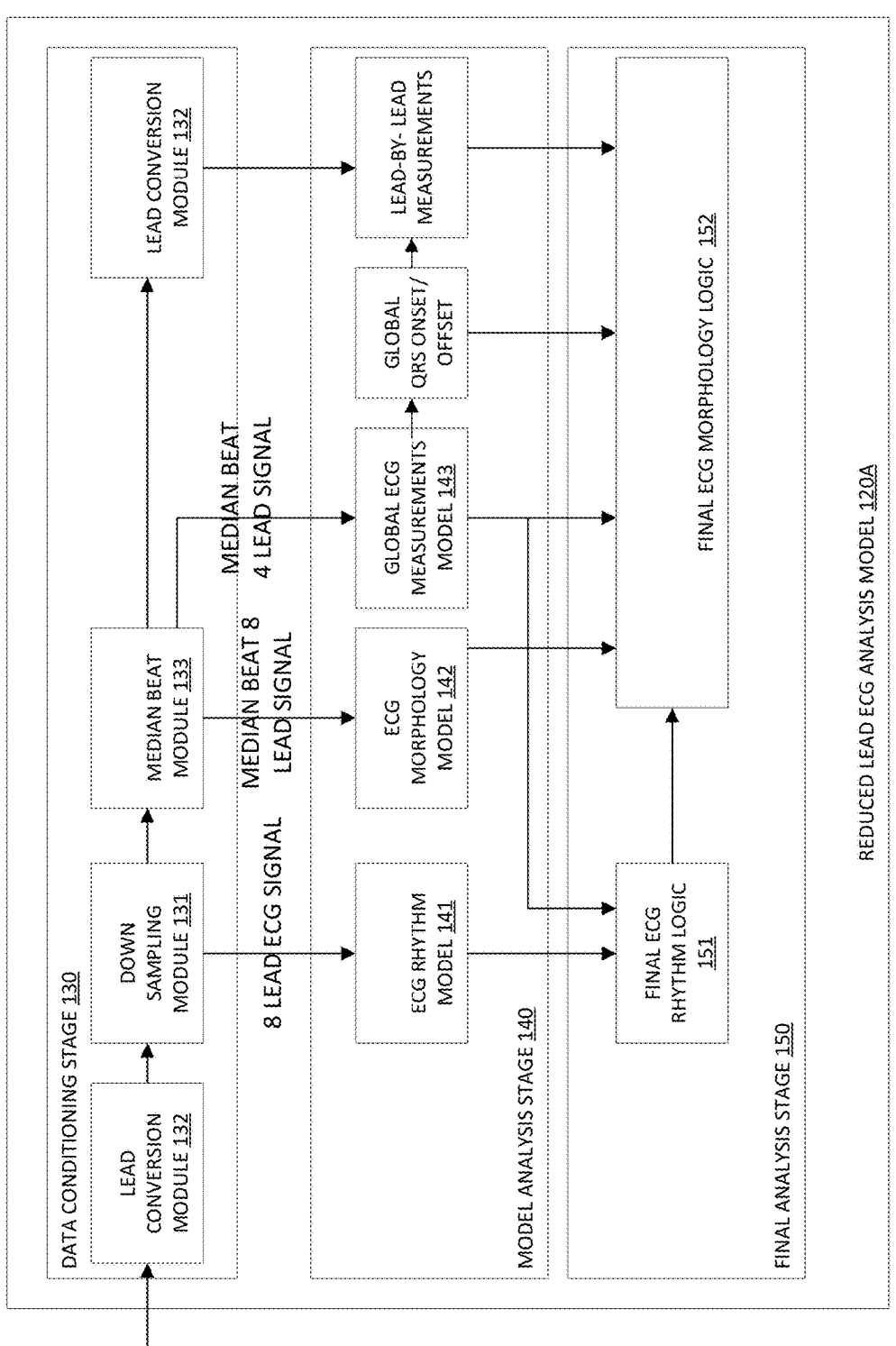
FIG. 4 is a block diagram illustrating the structure of machine learning (ML) model for performing reduced lead ECG interpretation, in accordance with some embodiments of the present disclosure.

The global ECG measurements model 143 may also estimate the global QRS onset/offset as shown in FIG. 4. The global ECG measurements model 143 may use the global QRS onset/offsets and the algorithmically derived 12 lead set to determine the lead-by-lead ECG measurements. In a standard resting 12-lead analysis, lead-by-lead ECG measurements are important in addition to the ECG global parameters described herein. Lead-by-lead measurements may include the amplitude, duration and the polarity of all major ECG morphology components including P wave, QRS complex, ST wave, and T wave. Since morphology determinations are mainly decided by the ECG morphology model 142, the final ECG morphology logic 152 may use the lead-by-lead ECG measurements to assist in the final classification, which reduces dependency on having accurate ECG measurements to a certain degree. Indeed, the lead-by-lead ECG measurements can help to prevent some obvious classification errors in case the ECG rhythm classification model 141, the ECG morphology model 142 and the global ECG measurements model 143 cannot capture them, or produce multiple classifications from which one needs to be selected. For example, during morphology classification, if the ECG morphology model 142 classifies both LBBB and Acute MI, the final ECG morphology logic 152 may make a final classification based on QRS duration, ST segment, and in some cases the T wave. In another example, during ECG rhythm analysis, a false positive classification of AFIB might be avoided by checking the P wave measurements including the PR interval and the P wave amplitude.

The final determination stage 150 may include logic to make correct exclusions/inclusions based on cardiology science and clinical practice. The final determination stage 150 may perform exclusion under various conditions. Since both the ECG rhythm classification model 141 and the ECG morphology model 142 are trained for non-exclusive multiclass classifications, it is possible that multiple abnormalities can be identified/classified. In some cases, multiple abnormal conditions can be identified for the same ECG, such as ischemia and infarction, or bundle branch blocks and ischemia. But in other cases, especially during ECG rhythm analysis, certain abnormalities can affect another abnormality's detection, or they can be mutually exclusive, like e.g., sinus rhythm and AFIB, or pace rhythm with sinus, etc. The final determination stage 150 may operate in one of two different modes: a high specificity mode and a high sensitivity mode. The high specificity mode may include a higher threshold for model output probability as well as more conditions based on lead-by-lead measurements. The high sensitivity mode may include a lower threshold for model output probability (e.g., 70%). In some embodiments, in high sensitivity mode, if the probability is very high (e.g., greater than 95%) then the model may immediately determine that the determined classification is the final classification.

As discussed herein, the final determination stage 150 may include final ECG rhythm logic 151 and final ECG morphology logic 152. The final ECG rhythm logic 151 may include logic to find a dominant rhythm from the following list: Paced rhythm, Sinus/Normal Sinus, Atrial fibrillation, Atrial flutter, Wide QRS tachycardia, Junctional rhythm, and Undetermined rhythm. If the dominant rhythm is sinus rhythm, then the final ECG rhythm logic 151 may attempt to find the associated sinus arrythmias. The input parameters to the final ECG rhythm logic 151 are as follows: The output of the ECG rhythm classification model 141, the global ECG measurements (PR interval, QRS duration, QT interval, and heart rate), and the R-R interval sequence of the dominant beats. All determinations of the final ECG rhythm logic 151 are made in 2 modes: High specificity, and high sensitivity as discussed above.

FIG. 9 illustrates the final ECG rhythm logic 151 as various sets of conditions for finding the dominant rhythm. The final ECG rhythm logic 151 may determine a pace rhythm as the dominant rhythm if the output of the ECG rhythm classification model 141 indicates that the probability of pace rhythm is high (e.g., greater than 0.8) and that the probability of pace rhythm is greater than the probability of any other rhythms. In addition, the heart rate must be less than 80 bpm, the QRS duration must be less than 150 ms, and the R-R variability must be small. If the pace rhythm is confirmed, the final ECG rhythm logic 151 may not perform any other checks for other rhythms.

The final ECG rhythm logic 151 may determine (i.e., confirm a sinus rhythm classification from the ECG rhythm classification model 141) a sinus rhythm as the dominant rhythm if the output of the ECG rhythm classification model 141 indicates that the probability of sinus rhythm is high (e.g., greater than 0.7) OR that the probability of a pace rhythm is less than the probability of other rhythms. In addition, the PR interval must be greater than 80 ms OR the probability of sinus rhythm must be is very high (e.g., greater than 0.95). Here, a proper range of PR interval indicate a valid P wave exist, which is the key feature for Sinus rhythm. This final analysis is to reinforce the DNN model's results. It should be noted that the specificity and sensitivity settings for sinus rhythms are opposite from other abnormal rhythms since a high specificity setting for another abnormal rhythm also means a higher sensitivity setting for the sinus rhythm. To emphasize this high specificity, a sinus rhythm is confirmed before other abnormal rhythms, except for the pace rhythm. If the ECG rhythm classification model 141 outputs a very high probability of sinus/normal sinus, the confirmation is made without checking for other rhythms.

The final ECG rhythm logic 151 may determine a Afib/Aflutter as the dominant rhythm if the output of the ECG rhythm classification model 141 indicates that the probability of Afib/aflutter is higher than other dominant rhythm (e.g., greater than 0.7) and the probability of pace rhythm is smaller than other rhythms. In addition, the PR interval must be less than 30 ms and there must be no valid P wave. If the probability (Afib) is less than the probability (aflutter), then the final ECG rhythm logic 151 may determine that aflutter is the dominant rhythm.

If the final ECG rhythm logic 151 rules out all other rhythms as the dominant rhythm, it may check if the junctional rhythm is the dominant rhythm based on whether there is a high probability of junctional rhythm from the ECG rhythm classification model 141 and a low R-R variation. If both of these conditions are met, then the final ECG rhythm logic 151 may determine that the junctional rhythm is the dominant rhythm.

If the final ECG rhythm logic 151 still has not determined a dominant rhythm after checking the junctional rhythm, it may check if there is a sinus rhythm using a more relaxed condition set. More specifically, the final ECG rhythm logic 151 may lower the threshold for probability of sinus rhythm to 0.6 and require that there be a valid P wave and that all global measurements are in their normal range (e.g., PR [120, 200], QRS duration<115, QTcF<460 ms).

In some embodiments, if the final ECG rhythm logic 151 confirms a sinus rhythm, it may attempt to determine one or more associated arrythmias are checked. More specifically, if there is a high probability of a 1st degree Atrial-Ventricular Conduction Block (AVB) and a PR interval greater than 220 ms, the final ECG rhythm logic 151 may determine that a 1st degree AVB is present. If there is a high probability of a 2nd degree AVB, the probability of the 2nd degree AVB is greater than the probability of the 3rd degree AVB, and the probability of the 2nd degree AVB is larger than other Marked arrhythmia probabilities, the final ECG rhythm logic 151 may determine that a 2nd degree AVB is present. If there is a high probability of a 3rd degree AVB, and the probability of the 3rd degree AVB is larger than other arrhythmia probabilities, the final ECG rhythm logic 151 may determine that a 3rd degree AVB is present. If there is a high probability of a Sinus bradycardia, and the heart rate is less than 50 bpm, the final ECG rhythm logic 151 may determine that a Sinus bradycardia is present. If there is a high probability of a Sinus Tachycardia, and the heart rate is greater than 100 bpm, the final ECG rhythm logic 151 may determine that a Sinus Tachycardia is present. If there is a high probability (e.g., greater than 0.8) of a marked (severe) sinus arrhythmia, the final ECG rhythm logic 151 may determine that a marked sinus arrhythmia is present.

The final ECG morphology logic 152 may include logic to reinforce the results of morphology DNN model and to improve the specificity of major morphology abnormality determinations. The ECG morphology model 142 also works in a nonexclusive mode, meaning multiple abnormal conditions can be classified for the same ECG. Although multiple conditions can happen physiologically, it might be helpful to focus on the main source of an abnormal condition, instead of multiple sources. For example, in acute myocardial infarction (Acute MI) interpretations, adding ST segment changes on top of the DNN model probability is a way to improve specificity. But if the bundle branch block, especially the left bundle branch block (LBBB) is confirmed, then the ST segment deflection can be secondary due to depolarization change, which can be difficult to differentiate from primary repolarization. Therefore, Acute MI final determination is not determined if LBBB or Pace ECG is confirmed.

The final ECG morphology logic 152 may make final morphology determinations based on the classifications from one or more of the ECG rhythm classification model 141 and the ECG morphology model 142 in following order: Pace ECG, RBBB, LBBB, Other Intra-Ventricular Blocks, LVH, RVH, Old MI, Acute MI, Other ST Elevation, Ischemia, Long QT, Atrial enlargement, Normal ECG. Each condition discussed below is general for both the high sensitivity and the high specificity modes, with only the thresholds being relatively different.

The final ECG morphology logic 152 may determine a pace ECG (i.e., confirm a pace ECG classification from the ECG morphology model 142) if both the ECG rhythm classification model 141 and ECG morphology model 142 indicate that the probability of a pace ECG is very high (e.g., greater than 0.95), and the R-R beat variation is small (RR_std/RR_mean is less than 0.04). If the final ECG morphology logic 152 confirms the pace ECG classification, it may skip performing checks for any other morphologies.

The final ECG morphology logic 152 may determine a RBBB (i.e., confirm a RBBB classification from the ECG morphology model 142 if the probability of RBBB indicated by the ECG morphology model 142 classification is high (e.g., greater than 0.8), and the QRS duration is greater than 120 ms, OR if the probability of RBBB indicated by the ECG morphology model 142 classification is greater than 0.95 and the QRS duration is greater than 110 ms. If the final ECG morphology logic 152 confirms the RBBB classification, it may skip performing checks for any other morphologies.

The final ECG morphology logic 152 may determine a LBBB (i.e., confirm a LBBB classification from the ECG morphology model 142) if the probability of LBBB indicated by the ECG morphology model 142 classification is high (e.g., greater than 0.8), and the QRS duration is greater than 125 ms OR, if the probability of LBBB indicated by the ECG morphology model 142 classification is greater than 0.95 and the QRS duration is greater than 115 ms. If the final ECG morphology logic 152 confirms the LBBB classification, it may skip performing checks for any other morphologies.

The final ECG morphology logic 152 may determine any other BBB (i.e., confirm a classification of any other BBB from the ECG morphology model 142) if the probability of such BBB indicated by the ECG morphology model 142 classification is high (e.g., greater than 0.8) and the QRS duration is greater than 115 ms OR, the probability of such BBB indicated by the ECG morphology model 142 classification is greater than 0.90 and the QRS duration is greater than 110 ms.

The final ECG morphology logic 152 may determine an LVH morphology (i.e., confirm an LVH classification from the ECG morphology model 142) if the probability of LVH indicated by the ECG morphology model 142 classification is very high (e.g., greater than 0.99) OR, if the probability of LVH indicated by the ECG morphology model 142 classification is high (e.g., greater than 0.9) and either one of the V leads has a QRS deflection greater than 2500 uV or the R_aVL is greater than 1000 uV (microvolts). It should be noted that LVH determinations usually require some ECG amplitude measurements. But since only 2 precordial leads are used, and the ECG is more aggressively lowpass filtered, the conventional amplitude criteria for LVH is not directly applied. Instead, the ECG morphology model 142 output is used in conjunction with a set of minimum amplitude and axis measurements checks. The final ECG morphology logic 152 may determine an RVH morphology (i.e., confirm an RVH classification from the ECG morphology model 142) if the probability of LVH indicated by the ECG morphology model 142 classification is very high (e.g., greater than 0.9) and the QRS axis is greater than 90 degrees.

The final ECG morphology logic 152 may determine an acute anterior MI morphology (i.e., confirm an acute anterior MI classification from the ECG morphology model 142) if the probability of acute anterior MI indicated by the ECG morphology model 142 classification is very high (e.g., greater than 0.95), at least one V lead has an ST greater than 200 uV and an ST/T ratio greater than 0.3, and at least one of the reciprocal lead (limb leads) has an ST less than −50 uV (ST depression). Alternatively, the final ECG morphology logic 152 may determine an acute anterior MI morphology if the probability of acute anterior MI is very high (e.g., greater than 0.99) and at least one V lead has an ST greater than 160 uV and an ST/T ratio greater than 0.3.

The final ECG morphology logic 152 may determine an acute inferior MI morphology (i.e., confirm an acute inferior MI classification from the ECG morphology model 142) if the probability of acute inferior MI indicated by the ECG morphology model 142 classification is very high (e.g., greater than 0.95), and at least one V lead has an ST greater than 100 uV and an ST/T ratio greater than 0.3. Alternatively, the final ECG morphology logic 152 may determine an acute inferior MI morphology if the probability of acute anterior MI is very high (e.g., greater than 0.99) and at least one inferior lead has an ST greater than 60 uV and an ST/T ratio greater than 0.3.

The final ECG morphology logic 152 may determine an acute lateral MI morphology (i.e., confirm an acute lateral MI classification from the ECG morphology model 142) if the probability of acute lateral MI indicated by the ECG morphology model 142 classification is very high (e.g., greater than 0.95), and at least one lateral lead has an ST greater than 100 uV and an ST/T ratio greater than 0.3. Alternatively, the final ECG morphology logic 152 may determine an acute lateral MI morphology if the probability of acute anterior MI is very high (e.g., greater than 0.99) and at least one lateral lead has an ST greater than 60 uV and an ST/T ratio greater than 0.3.

The final ECG morphology logic 152 may determine a previous myocardial infarction (old MI) morphology (i.e., confirm an old MI classification from the ECG morphology model 142) if the probability of old MI indicated by the ECG morphology model 142 classification is very high (e.g., greater than 0.90), and there is a significant Q wave.

The final ECG morphology logic 152 may determine an ischemia morphology (i.e., confirm an ischemia classification from the ECG morphology model 142) if the probability of ischemia indicated by the ECG morphology model 142 classification is very high (e.g., greater than 0.90), and there is a significant ST depression corresponding to the specification location calls in the lead groups: Anterior leads: ST in V2, V4; Inferior leads: II, III, aVF; lateral leads: I, aVL.

The final ECG morphology logic 152 may determine a prolonged QT morphology (i.e., confirm a prolonged QT classification from the ECG morphology model 142) if the probability of prolonged QT indicated by the ECG morphology model 142 classification is very high (e.g., greater than 0.90), and the QTcF (Corrected QT interval by Fridericia formula) is greater than 460 ms. The only exclusion condition for Prolonged QT is Paced ECG.

The final ECG morphology logic 152 may determine a normal morphology (i.e., confirm a normal classification from the ECG morphology model 142) if the ECG morphology model 142 did not detect any of the abnormal morphology conditions and rhythm conditions listed above, sinus rhythm is detected, the heart rate is higher than 50 bpm and lower than 90 bpm, the QRS duration is not longer than 120 ms, the PR interval is smaller than 230 ms, the QTcF is less than 460 ms, and the P, QRS and T axes are all larger than 0.

FIG. 10 is a flow diagram of a method 1000 for training and implementing an ML model for reduced lead set ECG interpretation, in accordance with some embodiments of the present disclosure. Method 1000 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the method 1000 may be performed by a computing device (e.g., computing device 101 illustrated in FIG. 3).

At block 1005, the ECG rhythm classification model 141 may be trained using any sufficiently large training data set. For example, the training data set may include 1 million labeled ECGs, with another 250K labeled ECGs for use as an independent test set. In the example of FIG. 6A, the batch size is 512, the learning rate is 0.001, and the drop rate 0.05. A total of 20 epochs are set. The final model is selected from the smallest validation error. A training weight matrix is used for balancing a large difference in prevalence among all determinations. For the lower prevalence determinations, a higher weight is used when the training error is backpropagated.

Referring also to FIG. 6, the convolution layers 610 may utilize a residual block structure that utilizes combinations of convolution layers and skip layers. A skip layer (also referred to as a skip connection or shortcut connections) may enable a residual block in the deep learning models to address the problem of vanishing and exploding gradients, which can occur when training very deep neural networks. This is done by adding the input of a layer directly to the output of one or more subsequent layers, creating a "shortcut" for the gradient to flow through. As a result, different parts of the convolution layers 610 will be trained at different rates for different training data points based on how the error flows backward through the layers of the convolution layers 610. FIG. 6 illustrates a residual block 610A, where a skip layer is used to skip the training of the convolution layer 2 during learning of an identity function X. ReLu may represent a nonlinear activation function.

In addition to the residual blocks, the ECG rhythm classification model 141 may include 2 dense layers 615 and 1 classification layer 620. In some embodiments, the ECG rhythm classification model 141 may further include a batch normalization layer and dropout layer for every residual block and dense layer to improve its robustness or generalization once it is trained (not every batch normalization and dropout layer shown in FIG. 6). The ECG rhythm classification model 141 is designed to classify rhythm determinations, examples of which are shown in table 1 (below). The classification layer 620 output may have both positive and negative probabilities for each determination. In some embodiments, for each of the 8 lead ECG signals (downsampled to 150 Hz), 9.5 seconds out of the 10 seconds of data is used for the input and the remaining 0.5 seconds of data may be used for augmentation with a time-shifting technique (random data shifting). This random data shifting is one of the data augmentation methods used to improve the generalization of the trained DNN models, which will result in the DNN models being less sensitive to the start and the end times of the input ECG rhythm data.

At block 1010, the ECG morphology model 142 may be trained with the same training data set as the ECG rhythm classification model 141 (which may include median beat data for each training ECG). In the example of FIG. 6A, the batch size is 512, the learning rate is 0.001, and the drop rate 0.05. A total of 20 epochs are set. The final model is selected from the smallest validation error. A morphology training weight matrix is also used for balancing a large difference in prevalence among all determinations. For the lower prevalence determinations, a higher weight is used when the training error is backpropagated. The ECG morphology model 142 is designed to classify ECG morphology determinations, examples of which are shown in table 2 (below). The classification layer of the ECG morphology model 142 has both positive and negative probabilities for each determination.

Referring also to FIG. 7A, the ECG morphology model 142 may capture morphology changes for each lead and relative changes from lead to lead, referred to as changes in the spatial domain. The ECG morphology model 142 may have a similar model structure as the ECG rhythm classification model 141, but with a smaller lead formation layer and fewer residual block layers, since the median beat 8 lead signal has a much shorter length than the 10 second duration of the 8 lead ECG signal input to the ECG rhythm classification model 141. In addition, all median beats are relatively aligned around their QRS onset. Another important design consideration for the Morphology model QRS region, is that the variations along the time axis are relatively smaller than rhythm signals.

To capture the spatial domain changes, the ECG morphology model 142 may form an ECG imaging by laying out of all the leads in a 2-D matrix/image pattern with the X-axis as time and the Y-axis as a lead order of [aVL, I, aVR, II, aVF, III, v2, v4], where the limb leads are reordered in a so-called Cabrera sequence. The ECG morphology model 142 may process the 2-D ECG signal matrix with a 2-D convolutional filter like in image classification cases. This method is more effective than applying multiple 1-D convolutional filters to each lead separately, which has been used by most other ECG training models. Since ECG is a projection of heart's electrical depolarization and repolarization process to the torso, a spatial 2-D signal matrix can capture this projection more effectively. Therefore, 2-D convolutional modes are applied to this ECG image input.

At block 1015, the global ECG measurements model 143 may be trained. The global ECG measurements model 143 measure ECG global parameters including PR interval, QRS duration, QT interval, and heart rate. These parameters are referred to as ECG global measurements because they are not lead-specific and are often estimated based on a combination of multiple leads. These parameters are often detected with complicated signal processing and feature detection algorithms based on domain knowledge. However, embodiments of the present disclosure estimate these ECG parameters using a deep learning model (the global ECG measurements model 143) applied to the median beat 8 lead signal generated from the 8 lead ECG signal. Because the ECG global parameters are closely related to ECG morphology, the global ECG measurements model 143 can be trained to perform a regression of the median beat 8 lead ECG signal to detect these parameters. Another aim of training the global ECG measurements model 143 is to also be able to identify the absence of a valid P wave as in atrial fibrillation cases.

FIG. 8 illustrates a detailed structure of the global ECG measurements model 143. The structure of the global ECG measurements model 143 is like the structure of the ECG morphology model 142 except the final classification layer of the global ECG measurements model 143 is replaced by a regression layer 820. In addition, the global ECG measurements model 143 does not have the batch normalization layers of the ECG morphology model 142 since they are more useful for classification than for regression. The global ECG measurements model 143 may receive as input a median beat 4 lead signal based on the lead set [I, II, v2, v4]. More specifically, the median beats generation module 133 may determine the median beats for each lead of the lead set [I, II, v2, v4] as discussed hereinabove and provide this median beat 4 lead signal to the global ECG measurements model 143. The global ECG measurements model 143 is trained to output three intervals: PR interval, QRS duration, and QT interval by minimizing the absolute error between labeled (physician-estimated) intervals from the training data and the model-estimated intervals.

At block 1020, ECG rhythm and ECG morphology classifications may be determined for an input ECG by the ECG rhythm classification model 141 and the ECG morphology model 142 respectively. At block 1025, the global parameters for the input ECG may be determined by the global ECG measurements model 143.

The final determination stage 150 may include final ECG rhythm logic 151 and final ECG morphology logic 152. At block 1030, the final ECG rhythm logic 151 may determine a dominant rhythm from the following list: Paced rhythm, Sinus/Normal Sinus, Atrial fibrillation, Atrial flutter, Wide QRS tachycardia, Junctional rhythm, and Undetermined rhythm. If the dominant rhythm is sinus rhythm, then the final ECG rhythm logic 151 may attempt to find the associated sinus arrythmias. The input parameters to the final ECG rhythm logic 151 are as follows: The output of the ECG rhythm classification model 141, the global ECG measurements (PR interval, QRS duration, QT interval, and heart rate), and the R-R interval sequence of the dominant beats. All determinations of the final ECG rhythm logic 151 are made in 2 modes: High specificity, and high sensitivity as discussed above.

The final ECG morphology logic 152 may make final morphology determinations based on the classifications from one or more of the ECG rhythm classification model 141 and the ECG morphology model 142 in following order: Pace ECG, RBBB, LBBB, Other Intra-Ventricular Blocks, LVH, RVH, Old MI, Acute MI, Other ST Elevation, Ischemia, Long QT, Atrial enlargement, Normal ECG. Each condition discussed below is general for both the high sensitivity and the high specificity modes, with only the thresholds being relatively different. The input parameters to the final ECG morphology logic 152 are as follows: the output of the ECG morphology model 142, the output of the ECG rhythm classification model 141 (in some cases), and the global ECG measurements (PR interval, QRS duration, QT interval, and heart rate).

Figure 11:
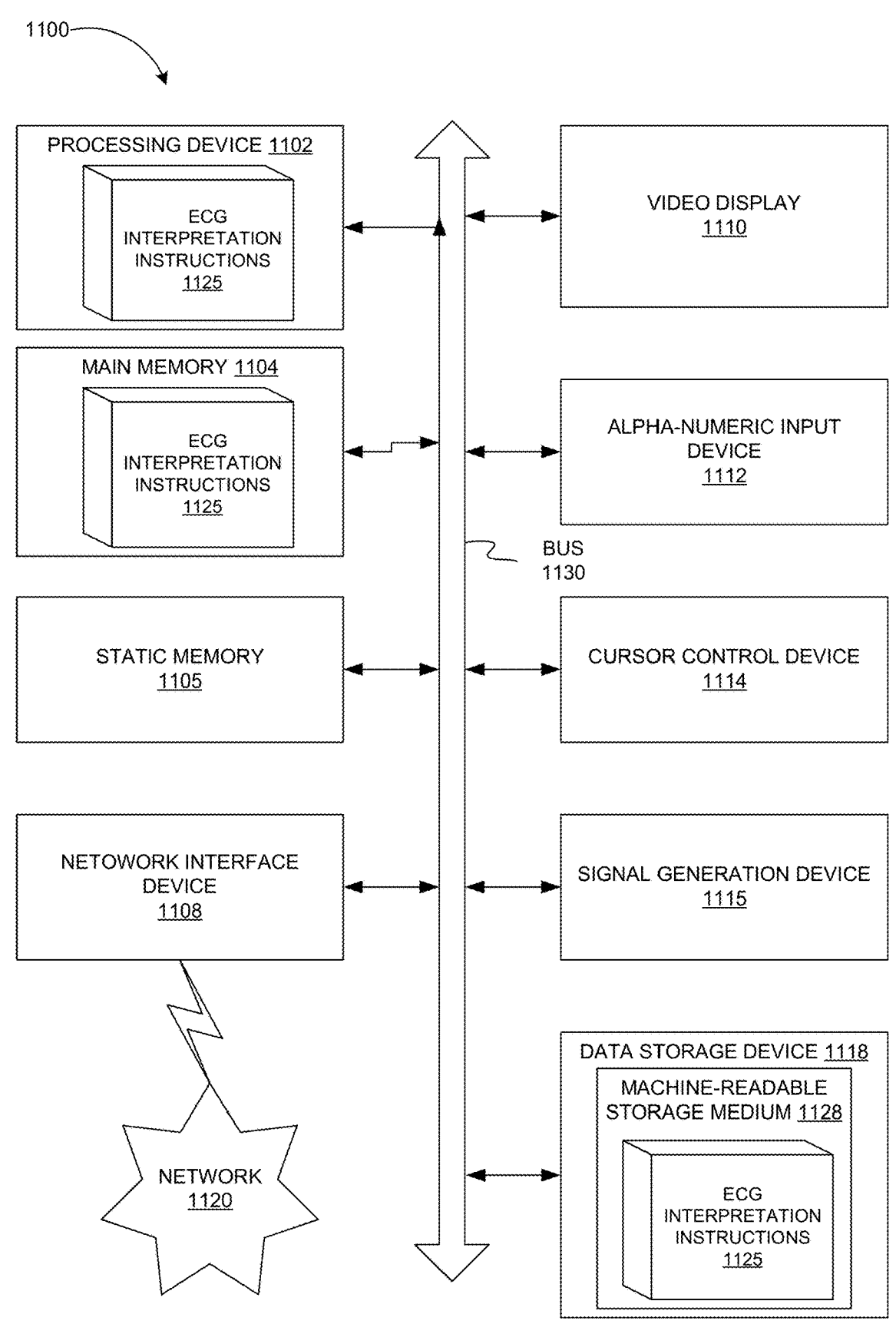
FIG. 11 is a block diagram of an example computing device that may perform one or more of the operations described herein, in accordance with some embodiments of the present disclosure.

FIG. 11 illustrates a diagrammatic representation of a machine in the example form of a computer system 1100 within which a set of instructions, for causing the machine to perform any one or more of the methodologies discussed herein for performing reduced lead ECG interpretation.

In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, a switch or bridge, a hub, an access point, a network access control device, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. In one embodiment, computer system 1100 may be representative of a server.

The exemplary computer system 1100 includes a processing device 1102, a main memory 1104 (e.g., read-only memory (ROM), flash memory, dynamic random access memory (DRAM), a static memory 1106 (e.g., flash memory, static random access memory (SRAM), etc.), and a data storage device 1118, which communicate with each other via a bus 1130. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Computing device 1100 may further include a network interface device 1108 which may communicate with a network 1120. The computing device 1100 also may include a video display unit 1110 (e.g., a liquid crystal display (LCD) or a cathode ray tube (CRT)), an alphanumeric input device 1112 (e.g., a keyboard), a cursor control device 1114 (e.g., a mouse) and an acoustic signal generation device 1116 (e.g., a speaker). In one embodiment, video display unit 1110, alphanumeric input device 1112, and cursor control device 1114 may be combined into a single component or device (e.g., an LCD touch screen).

Processing device 1102 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 1102 may also be one or more special-purpose processing devices such as an application specific integrated circuit (ASIC), a field programmable gate array (FPGA), a digital signal processor (DSP), network processor, or the like. The processing device 1102 is configured to execute instructions 1125, for performing the operations and steps discussed herein.

The data storage device 1115 may include a machine-readable storage medium 628, on which is stored one or more sets of instructions 1125 (e.g., software) embodying any one or more of the methodologies of functions described herein. The instructions 1125 may also reside, completely or at least partially, within the main memory 1104 or within the processing device 1102 during execution thereof by the computer system 1100; the main memory 1104 and the processing device 1102 also constituting machine-readable storage media. The instructions 1125 may further be transmitted or received over a network 1120 via the network interface device 1108.

While the machine-readable storage medium 1128 is shown in an exemplary embodiment to be a single medium, the term "machine-readable storage medium" should be taken to include a single medium or multiple media (e.g., a centralized or distributed database, or associated caches and servers) that store the one or more sets of instructions. A machine-readable medium includes any mechanism for storing information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Additionally, some embodiments may be practiced in distributed computing environments where the machine-readable medium is stored on and or executed by more than one computer system. In addition, the information transferred between computer systems may either be pulled or pushed across the communication medium connecting the computer systems.

Embodiments of the claimed subject matter include, but are not limited to, various operations described herein. These operations may be performed by hardware components, software, firmware, or a combination thereof.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

It will be appreciated that variants of the above-disclosed and other features and functions, or alternatives thereof, may be combined into may other different systems or applications. Various presently unforeseen or unanticipated alternatives, modifications, variations, or improvements therein may be subsequently made by those skilled in the art which are also intended to be encompassed by the following claims. The claims may encompass embodiments in hardware, software, or a combination thereof.

What is claimed is:

1. A method comprising:
training a first deep neural network (DNN) to classify electrocardiogram (ECG) rhythm characteristics, wherein a training weight matrix is used to balance a difference in prevalence among classifications during training;
training a second DNN to classify ECG morphology characteristics;
training a third DNN to identify global ECG parameters, wherein both the first and second DNNs comprise a classification layer and the third DNN comprises a regression layer; and
implementing the first, second, and third DNNs as an ensemble DNN for ECG interpretation.

2. The method of claim 1, further comprising:
in response to receiving an ECG:
classifying rhythm characteristics of the ECG using the first DNN;
classifying morphology characteristics of the ECG using the second DNN; and
identifying global parameters of the ECG using the third DNN; and
applying a set of decision logic to the ECG rhythm characteristics and the ECG morphology characteristics to diagnose one or more conditions indicated by the ECG based at least in part on the ECG global parameters.

3. The method of claim 2, wherein the set of decision logic comprises:
a first set of criteria for validating the classification of the rhythm characteristics of the ECG based at least in part on the global parameters of the ECG; and
a second set of criteria for validating the classification of the morphology characteristics of the ECG based at least in part on the global parameters and the validated classification of the rhythm characteristics of the ECG.

4. The method of claim 1, wherein:
the classification of the rhythm characteristics of the ECG comprises a probability for each of a set of rhythms; and
the classification of the morphology characteristics of the ECG comprises a probability for each of a set of morphologies.

5. The method of claim 4, wherein one or more of the first, second and third DNN comprise convolution neural networks (CNNs).

6. The method of claim 5, further comprising:
using a random data shifting technique to further generalize each of the first, second and third DNNs.

7. The method of claim 1, wherein each of the first, second and third DNNs comprises a convolution block having a residual block structure that combines a set of convolution layers and a set of skip layers.

8. A system comprising:
an electrocardiogram (ECG) monitor configured to perform an ECG of a person and transmit the ECG; and
a computing device configured to:
    in response to receiving the ECG from the ECG monitor:
        classify rhythm characteristics of the ECG using a first deep neural network (DNN), wherein the first DNN is structured to classify rhythm characteristics of ECG data and wherein a training weight matrix is used to balance a difference in prevalence among classifications during training of the first DNN;
        classify morphology characteristics of the ECG using a second DNN, wherein the second DNN is structured to classify morphology characteristics of ECG data; and
        identify global parameters of the ECG using a third DNN, wherein the third DNN is structured to identify global parameters of ECG data; and
    apply a set of decision logic to the ECG rhythm characteristics and the ECG morphology characteristics to diagnose one or more conditions indicated by the ECG based at least in part on the ECG global parameters.

9. The system of claim 8, wherein the processing device is further to:
train the first deep neural network (DNN) to classify electrocardiogram (ECG) rhythm characteristics;
training the second DNN to classify ECG morphology characteristics;
training the third DNN to identify global ECG parameters, wherein both the first and second DNNs comprise a classification layer and the third DNN comprises a regression layer.

10. The system of claim 8, wherein:
the classification of the rhythm characteristics of the ECG comprises a probability for each of a set of rhythms; and
the classification of the morphology characteristics of the ECG comprises a probability for each of a set of morphologies.

11. The system of claim 10, wherein one or more of the first, second and third DNN comprise convolution neural networks (CNNs).

12. The system of claim 11, wherein the processing device is further to:
use a random data shifting technique to further generalize each of the first, second and third DNNs.

13. The system of claim 8, wherein the set of decision logic comprises:
a first set of criteria for validating the classification of the rhythm characteristics of the ECG based at least in part on the global parameters of the ECG; and
a second set of criteria for validating the classification of the morphology characteristics of the ECG based at least in part on the global parameters and the validated classification of the rhythm characteristics of the ECG.

14. The system of claim 8, wherein each of the first, second and third DNNs comprises a convolution block having a residual block structure that combines a set of convolution layers and a set of skip layers.

15. A non-transitory computer-readable medium having instructions stored thereon which, when executed by a processing device, cause the processing device to:
train a first deep neural network (DNN) to classify electrocardiogram (ECG) rhythm characteristics, wherein a training weight matrix is used to balance a difference in prevalence among classifications during the training of the first DNN;
train a second DNN to classify ECG morphology characteristics;
train a third DNN to identify global ECG parameters;
in response to receiving an ECG:
    classify rhythm characteristics of the ECG using the first DNN, wherein the first DNN is structured to classify rhythm characteristics of ECG data;
    classify morphology characteristics of the ECG using the second DNN, wherein the second DNN is structured to classify morphology characteristics of ECG data; and
    identify global parameters of the ECG using the third DNN, wherein the third DNN is structured to identify global parameters of ECG data; and
apply a set of decision logic to the ECG rhythm characteristics and the ECG morphology characteristics to diagnose one or more conditions indicated by the ECG based at least in part on the ECG global parameters.

16. The non-transitory computer-readable medium of claim 15, wherein:
the classification of the rhythm characteristics of the ECG comprises a probability for each of a set of rhythms; and
the classification of the morphology characteristics of the ECG comprises a probability for each of a set of morphologies.

17. The non-transitory computer-readable medium of claim 15, wherein the set of decision logic comprises:
a first set of criteria for validating the classification of the rhythm characteristics of the ECG based at least in part on the global parameters of the ECG; and
a second set of criteria for validating the classification of the morphology characteristics of the ECG based at least in part on the global parameters and the validated classification of the rhythm characteristics of the ECG.

18. The non-transitory computer-readable medium of claim 17, wherein one or more of the first, second and third DNN comprise convolution neural networks (CNNs).

19. The non-transitory computer-readable medium of claim 17, wherein the processing device is further to:
use a random data shifting technique to further generalize each of the first, second and third DNNs.

20. The non-transitory computer-readable medium of claim 15, wherein each of the first, second and third DNNs comprises a convolution block having a residual block structure that combines a set of convolution layers and a set of skip layers.

* * * * *